United States Patent
Kaufmann et al.

(10) Patent No.: US 6,566,063 B1
(45) Date of Patent: May 20, 2003

(54) METHODS FOR DETERMINING METASTATIC POTENTIAL OF BREAST CANCER CELLS BY DETECTING GSEF GENE PRODUCT EXPRESSION

(75) Inventors: Joerg Kaufmann, Berlin (DE); Hong Xin, La Jolla, CA (US); Greg Harrowe, Berkeley, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/570,593

(22) Filed: May 12, 2000

Related U.S. Application Data

(60) Provisional application No. 60/134,112, filed on May 14, 1999.

(51) Int. Cl.$^7$ ............................ C12Q 1/68; C12P 19/34; C07H 21/02; C07H 21/04
(52) U.S. Cl. ........................ 435/6; 435/91.2; 536/23.5; 536/24.31; 536/24.33
(58) Field of Search ........................ 435/6, 7.1; 514/44; 536/23.5

(56) References Cited

U.S. PATENT DOCUMENTS 5,721,113 A  2/1998  Libermann et al.

FOREIGN PATENT DOCUMENTS

| EP | 0 839 908 A2 | 5/1998 | |
|----|--------------|--------|---|
| WO | WO 98/23782 | 6/1998 | |
| WO | WO 00/06589 | 2/2000 | |
| WO | WO01/42472 A2 * | 6/2001 | ............ C12N/15/12 |

OTHER PUBLICATIONS

Bochert et. al Biochemical and Biophysical Research Communications 246, 176–181(1998).*
Liotta, LA Scientific American, pp 54–63, Feb. 1992.*
Liu et. al The Prostate 30:145–153 (1997)).*
Liu et al. (1997), "Identification of Differentially Expressed Prostate Genes: Increased Expression of Transcription Factor ETS-2 in Prostate Cancer." *The Prostate*, vol. 30(3):145–153.
Oettgen et al. (2000), "PDEF, a Novel Prostate epithelium–specific Ets Transcription Factor, Interacts with the Androgen Receptor and Activates Prostate–specific Antigen Gene Expression." *J. Biol. Chem.*, vol. 275(2):1216–1225.
Sementchenko et al. (1998), "ETS2 function is required to maintain the transformed state of human prostate cancer cells." *Oncogene*, vol. 17(22):2883–2888.
Database EML –online (2000), SIMS: "HTG; HTGS_DRAFT; HTGS_PHASE1."
Database EMBL –online (1999), Oettgen et al.: "ETS Transcription Factor."
"Promoterfinder" (1996/97) *Clontech*, p. 56.

(List continued on next page.)

*Primary Examiner*—Carla J. Myers
*Assistant Examiner*—Sally Sakelaris
(74) *Attorney, Agent, or Firm*—Carol L. Francis; Kimberlin L. Morley; Robert P. Blackburn

(57) ABSTRACT

The invention features methods for detection of metastatic and potentially metastatic cancerous cells by detection of expression of a gland-specific Ets transcription factor (GSEF) sequence, which encodes an Ets-domain containing protein. The invention also features methods and compositions for modulation of the polypeptide and/or gene activity for prophylactic and therapeutic purposes, such as inhibition of progression of a cell to a metastatic cancerous cell.

12 Claims, 14 Drawing Sheets

OTHER PUBLICATIONS

Barsky, et al., "*Evidence of a dominant transcriptional pathway which regulates an undifferentiated and complete metastic phenotype*," Oncogene 15: 2077–2091 (1997).

Bochert, et al., "*Molecular Cloning and Expression of Ehf, a New Memmber of the ets Transcription Factor/Oncoprotein Gene Family*," Biochemical and Biophysical Research Communications 246, 176–181 (1998).

Chang, et al., "*ESX: a structurally unique Ets overexpressed early during human breast tumorigenesis*," Oncogene 14: 1617–1622 (1997).

Choi, et al., "*A Novel ets–related Transcription factor, ERT/ESX/ESE–1, Regulatres Expression of the Transforming Groeth Factor–β Type II Receptor*," The Journal of Biological Chemistry vol. 273 110–117 (Jan. 2, 1998).

Mishra, et al., "*Elf3 encodes a novel 200–kd β–spectrin: role in liver development*," Oncogene 18: 353–364 (1999).

Neve, et al., "*The epithelium–specific Ets transcription factor ESX is associated with the mammary gland development and involution*," FASEB Journal vol. 12 No. 14 1541–1550 (Nov. 1998).

Nozawa, et al., "*Prostate–specific Transcription Factor hPSE is Translated Only in Normal Prostate Epithelial Cells*," Cancer Research 60 1348–1352 (Mar. 2000).

Oettgen , et al., "*Genomoc Organization of the Human ELF3 (ESE–1/ESX) Gene, A member if the Ets Transcription Factor Family, and Identification of a Functional Promoter*," Genomics 55, 358–362 (1999).

Ottegen, et al., "*The Novel Epithelia–Specific Ets Transcription Factor Gene ESX Maps to Human Chromosome 1q32.1*," Genomics 45,456–457 (1997).

Sharrocks, et al., "*The ETS–domain Transcription Factor Family*," Int. J. Biochem Cell Biol. vol. 29 No. 12 1371–1387 (1997).

Tymms, et al., "*A novel epithelia–expressed ETS gene, ELF3: human and murine cDNA sequences, murine genomic organization, human mapping to 1q32.2 and expression in tissues and cancer*," Oncogene 15: 2449–2462 (1997).

Welch, et al., *Microcell–mediated transfer of chromosome 6 into metastatic human C8161 melanoma cells suppresses metastasis but does not inhibit tumorigenicity*, 'Oncogene 9, 255–262 (1994).

Yamada, et al., "*Cloning and expression of the mouse Pse gene encoding a novel Ets family member*," Gene 241, 267–274 (2000).

GenBank Accession No. AA662164, deposited Dec. 3, 1997.

GenBank Accession No. AB031549, deposited Jan. 20, 2000.

GenBank Accession No. AF071538, deposited Jan. 10, 2000.

GenBank Accession No. NM_012391, deposited Nov. 2, 2000.

GenBank Accession No. U66894, deposited May 21, 1997.

GenBank Accession No. U73843, deposited Aug. 6, 1997.

GenBank Accession No. U97156, deposited Dec. 5, 1997.

GenBank Accession No. AF017307, deposited Aug. 21, 1997.

GenBank Accession No. NM_004433, deposited May 7, 1999.

GenBank Accession No. AF016295, deposited Jan. 16, 1998.

GenBank Accession No. U73844, deposited Aug 6. 1997.

GenBank Accession No. NM_007921, deposited Jan. 4, 2000.

GenBank Accession No. AF016294, deposited Jan. 16, 1998.

GenBank Accession No. AF110184, deposited Jul. 22, 1999.

GenBank Accession No. AF071538, deposited Dec. 13, 1998.

* cited by examiner

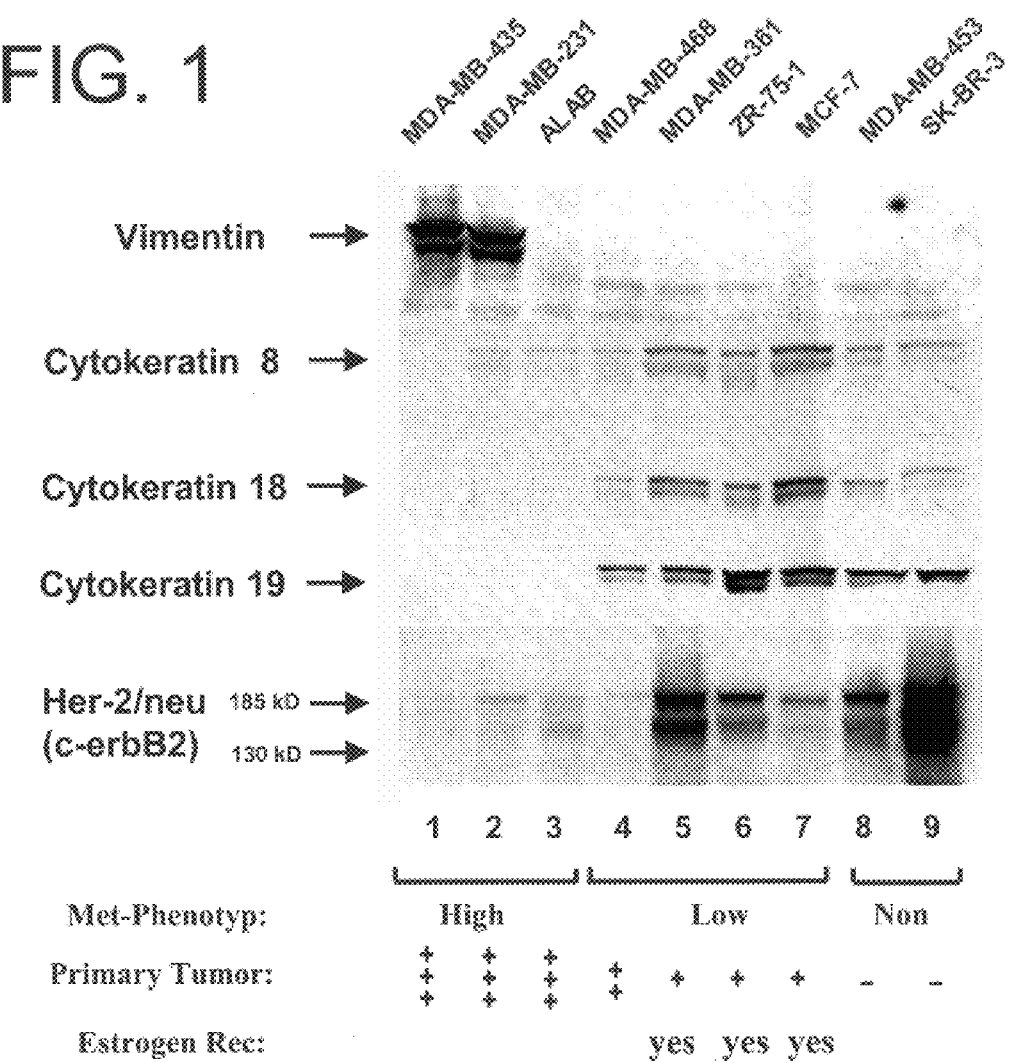

FIG. 2A

```
-1380  GATACAGTAGTGCCTGTTAAGCAGTGGTCATTAGTATTAATGCATCAGAATGCTGTGATATAAGCCAGGCTTCTGTGAGAGTGGGGAGG
-1290  AGGGAGGCGTGGCCACCAGAGAAGCAGGCACAAAAACGCACTCTAGGGGAAGGAGATCCACCTGGAAACGCAGCGTGTCTTTCTTTATTG
-1200  ACCCTGGAGGGCTGACCATTGGGGATTAGGAGTGGTCGAGTGTACCATTCAGGACCTTGTGTTACCTCCCCTTCCTCCGCTCCATCCT
-1110  CCCTCAACCTTCTCGGGAATGACTGGAGAATGTGGTATTGGTGAAGGTGAGGGCTAGTTCTAAAGGCCTTGAGATCCCCTGCAGCCCAGAA
-1020  GCAAAGTGCAACCTTACGTTGGAGAATGTGGTATTGGTGAAGGTGAGGGCTAGTTCTAAAGGCCTTGAGATCCCCTGCAGCCCAGAA
-930   TCCTCATGCTCTCGGCAGTTACACAGTTACTCCTGAAACAAGAGAAAAATCAGCATTATCTAGAACTTTCTCCCGTCAGAATGGAGGTAG
-840   CAGGTACGTGGAGCCCTTCTGAGATGATTTGGAGAGAAAGGAAGGCCCAGCCTCCAGGACAACTCTCAGCCACCTGGCAGGACATGGAGG
-750   AAGCCAAAAGCTGGACTGTGTGGCCCCGCAGGGCTCAAGGAGGTCAGGAGCCAAGTGCTGCTGACTGGCCCCCGATTACAGCCTGGGTATCTCTGTCC
-660   TGCATGGCATCCCTGCCATCACCCTTTGGGCTATGGGAGGTCTGCATGTGTGCTGCTGGGCACAGAGACCCTGTGGGCCTGCACTGGGGCACACAGTTCCCACCAGTCGCGGTTGG
-570   AGGAGTCCTTCCTCACCGCCACTGTGTGACAGGTCTGCATGAAGCTCTCTGAAGCTCTCTCCCCCTCAGTCCTCCATCGGGCATGGTGGTTCTGATCTCCACTGCTGCTC
-480   CCCACAAGCCTCGGGATCCCTCCCCAGGGTTCTCACCCTGTGTGCCCCCTCAGTGCCCCCTCAGTCCTCCATCGGGCATGGTGGTTCTGATCTCCACTGCTGCTC
-390   CTCAACTGATTTCCTCTCTGGCCCCCTCAGTCTGATCCATCTTAGAACCCCAGCCTGATCCATCTTAGAACCCCAGCCTGATCTCTGGCGCCTTGCACGTAATATG
-300   ACTTGTCTGTCTCTGGCCCCCTCAGTCTGATCCATCTTAGAACCCCAGCCTGATCTCTGGCGCCTTGCACGTAATATG
-210   AGCTGAGTGGCTATGCAGCAACCAATGAACGAGTGAGTGAATGAGTGAGCGAGTCCCCTAGCTGTCAGGCATGATCCCCCAGCA
-120   AGGAGGGGAGACCTGCAAGGGTTAATCAGGGCCTGCCTGTGTCTGAGGTAAGCAAGGAGTGTATTGTTCAGGTAAATAAGGAAGGA
                                                          +1
-30    TTACTTATAATGGGAAATCAGGCCCTGACCAACTCTTCATCTCGCGGCTGTCTGACTTCCTCCCAGCACATTCCTCGCACTCTGCCGTGTC
       TATAA
+61    CACACTGCCCCACAGACCCAGTCCTCCAAGCCCTGCTGCCAGCTCCCTGCAAGCCCCTCAGGTTGGCCTTGCCACGGTGCCAGCAGGCAG
+151   CCCTGGGCTGGGGGTAGGGGACTCCCTACAGGGACTCCCTACAGGGACTCAGAGGGCCACCCTTGAGGGTGGCCAGGCCCCCAGTGGC
+241   CAACCTGAGTGCTGCCTCTGCCAGCACCCTGCCACCAGCAGCCCTGGTTCCGCTGCTGCCCTGGCCCTGAGACACGCCAGTGCCTCA
+331   GCTGCCCACACCCTTCCCGGCCCCCTGAAGTTGGCACTGCAGCAGTCCTGCAGCAGTGGCACTGCAGCAGTGGCACTGCAGACCAGCAGCACAGACAGCCGCCAGCC
```

FIG. 2B

```
          M  G  S  A  S  P  G  L  S  S  V  S  P  S  H  L  L  L  P  P  D  T  V  S  R >
 +421 CAAACAGCAGCGGCATGGGCAGCGCCAGCCCGGGTCTGAGCAGCGTATCCCCAGCCACTCCTGCCCCCGACACGTGTCGCGGA
      T  G  L  E  K  A  A  G  A  V  G  L  E  R  R  D  W  S  P  S  P  P  A  T  P  E  Q  G  L >
 +511 CAGGCTTGGAGAAGGCGGCAGGCGCAGTGGGTCTGGAGAGACGGGACTGGAGTCCAGTCCACCGCCACCCGAGCAGGGCCTGT
      S  A  F  Y  L  S  Y  F  D  M  L  Y  P  E  D  S  S  W  A  A  K  A  P  G  A  S  S  R  E  E >
 +601 CCGCCTTCTACCTCTCCTACTTTGACATGCTGTACCCTGAGGACAGCAGCTGGGCAGCCAAGGCCCCTGGGGCCAGCAGTCGGGAGGAGC
      P  P  E  E  P  E  Q  C  P  V  I  D  S  Q  A  P  A  G  S  L  D  L  V  P  G  G  L  T  L  E >
 +691 CACCTGAGGAGCCTGAGCAGTGCCCCGGTCATTGACAGCCAGGCCCCAGCGGGCAGCCTGGACTTGGTGCCCGGGGGCTGACCTTGGAGG
      E  H  S  L  E  Q  V  Q  S  M  V  V  G  E  V  L  K  D  I  E  T  A  C  K  L  L  N  I  T  A >
 +781 AGCACTCGCTGGAGCAGGTGCAGTCCATGGTGGTGGGCGAAGTGCTCAAGGACATCGAGACGGCCTGCAAGCTGCTCAACATCACCGCAG
      D  P  M  D  W  S  P  S  N  V  Q  K  W  L  L  W  T  E  H  Q  Y  R  L  P  P  M  G  K  A  F >
 +871 ATCCCATGGACTGGAGCCCCAGCAATGTGCAGAAGTGGCTCCTGTGGACAGAGCACCAATACCGGCTGCCCCCCATGGGCAAGGCCTTCC
      Q  E  L  A  G  K  E  L  C  A  M  S  E  E  Q  F  R  Q  R  S  P  L  G  G  D  V  L  H  A  H >
 +961 AGGAGCTGGCCGGGAAGGAGCTGTGCGCCATGTCGGAGGAGCAGTTCCGCCAGCGCTCGCCCCTGGGTGGAGATGTGCTCACGCCCACC
      L  D  I  W  K  S  A  A  W  M  K  E  R  T  S  P  G  A  I  H  Y  C  A  S  T  S  E  E  S  W >
+1051 TGGACATCTGGAAGTCAGCGGCCTGGATGAAAGAGCGGACTTCACCTGGGGCGATTCACTCTGTCCTCGACCAGTGAGGAGAGCTGGA
      T  D  S  E  V  D  S  S  C  S  G  Q  P  I  H  L  W  Q  F  L  K  E  L  L  L  K  P  H  S  Y >
+1141 CCGACAGCGAGGTGGACTCATCATGTCTCCGGGCAGCCCATCCACCTGTGGCAGTTCCTCAAGGAGTTGCTACTCAAGCCCCACAGCTATG
      G  R  F  I  R  W  L  N  K  E  K  G  H  F  K  I  H  E  D  S  A  Q  V  A  R  L  W  G  I  R  K >
+1231 GCCGCTTCATTAGGTGGCTCAACAAGGAGAAGGGCATCTTCAAAATTCACGAAGACTCAGCCCAGGTGGCCCGCCTGTGGGGCATCCGCAAGA
      N  R  P  A  M  N  Y  D  K  L  S  R  S  I  R  Q  Y  Y  Y  K  K  G  I  I  R  K  P  D  I  S  Q >
+1321 ACCGTCCCGCCATGAACTACGACAAGCTGAGCCGCTCAATCCGCCAGTATTACGAAGAAGGGCATCATCCGAAGCCAGACATCTCCCAGC
      R  L  V  Y  Q  F  V  H  P  I  *
+1411 GCCTCGTCTACCAGTTCGTGCACCCCATCTGAGTGCCTGGCCCTGCCCTCTCTCCTGCCCTGCC
+1501 TCAGCCAGGCCCTGAGATGGGGAAAACGGGCAGTCTGCTTCCAGAGCCTTCGACCTTCAGGAGGGCAACCAACTG
+1591 CCCCAGGGGATATGGTCCTCCCAACACCTGCTCCCCAGCATTCCTGACCCTGCCTCCATCCCTGCCTCCCCTGACGGGCACC
+1681 GGGAGACAGGGCTGCTCCAGGCCTACAGAGCAGCCTGCCATGGTGCAGGGAGACATCTGCACCCCTGAG
+1771 AGGCAGTCCAGGAGTGCCCCAGGAATGATAATAGAGATACTAGAGACTGAAAAAAAAAAAAAAAAAAA
+1861 TTGGGCAGCCAGGAGTGCCCCGGA                                           +1938
```

C7= prostate
D7= salivary gland
D8= mammary gland
C8= stomach
C4= colon
F3= trachea
H3/4= control

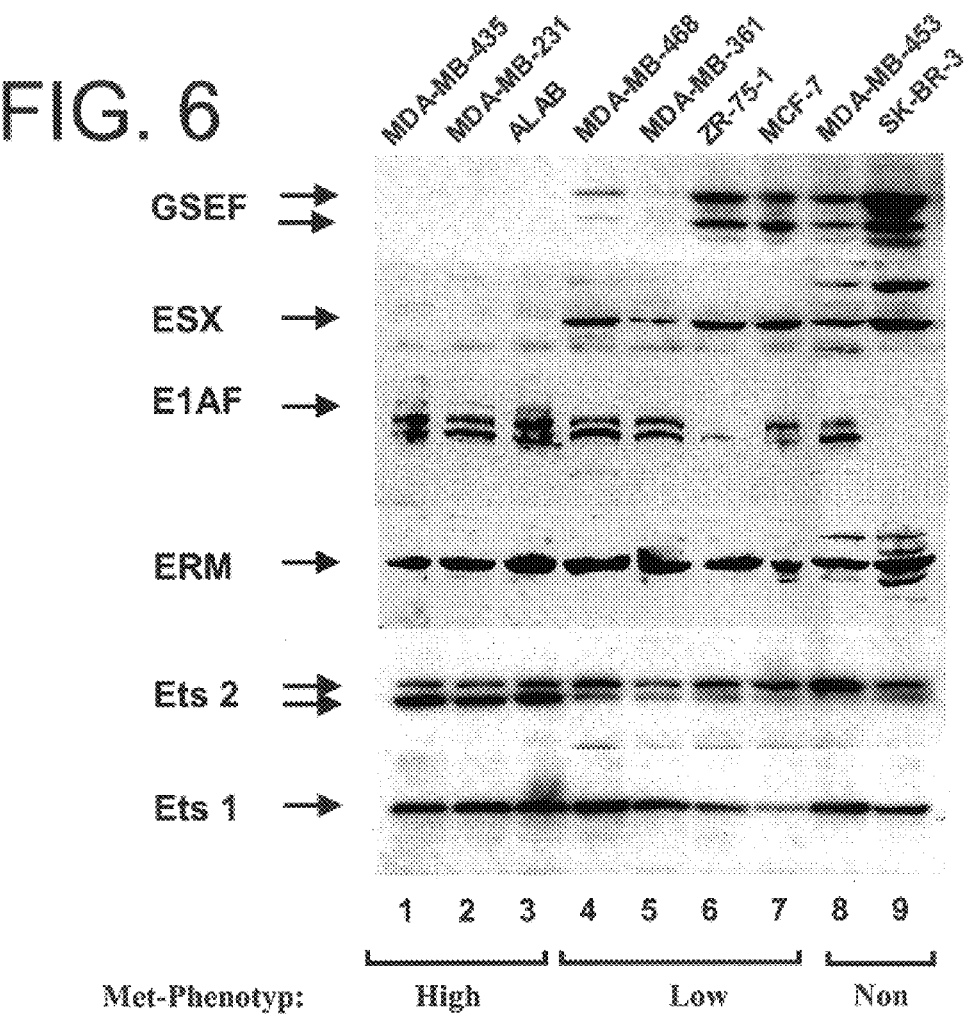

FIG. 11
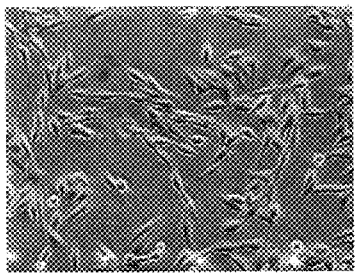
Parental MDA-MB-435
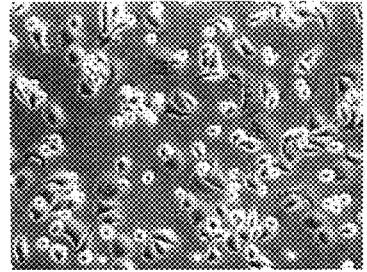
SK-BR-3
MDA-MB-435-E1AF (Cl.43)
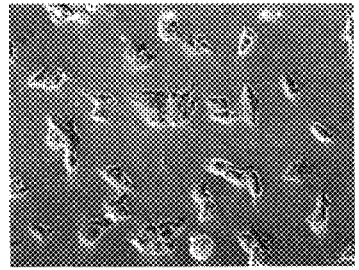
MDA-MB-435-GSEF (Cl.46)
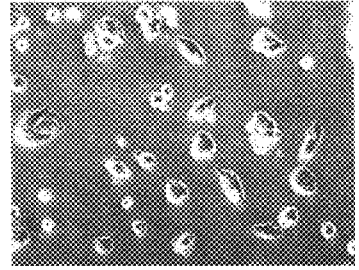
MDA-MB-435-GSEF (Cl.48)

FIG. 12
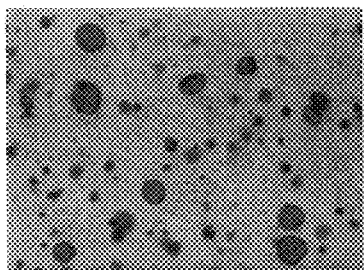
Parental MDA-MB-435
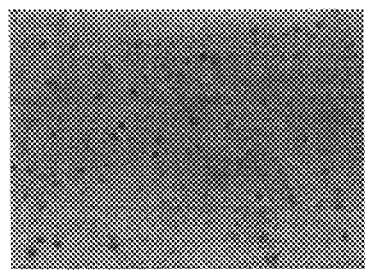
SK-BR-3
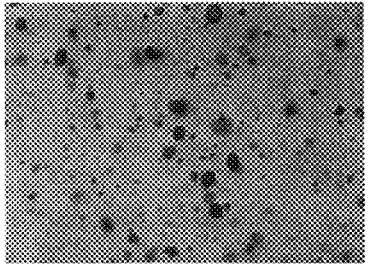
MDA-MB-435-E1AF (Cl.43)
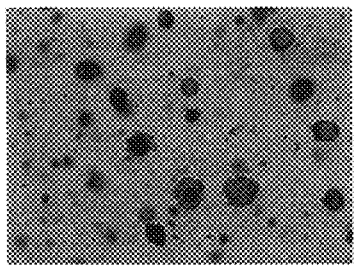
MDA-MB-435-GSEF (Cl.46)
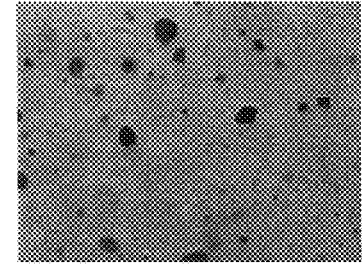
MDA-MB-435-GSEF (Cl.48)

FIG. 13
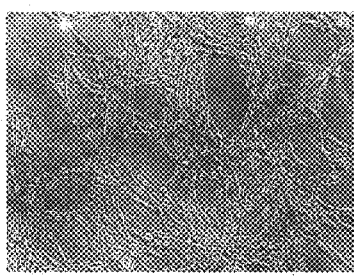
Parental MDA-MB-435
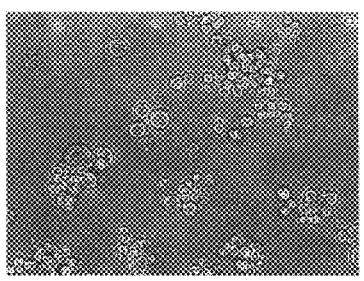
SK-BR-3
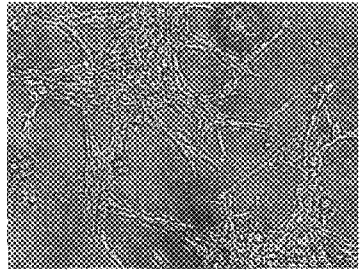
MDA-MB-435-E1AF (Cl.43)
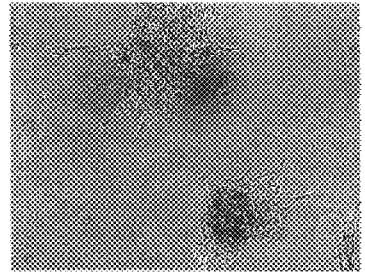
MDA-MB-435-GSEF (Cl.46)
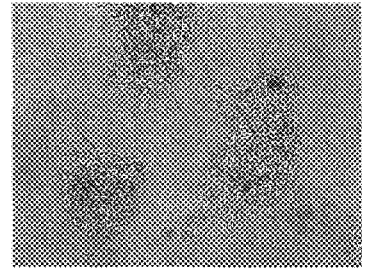
MDA-MB-435-GSEF (Cl.48)

SEQUENCE LISTING

```
<160> NUMBER OF SEQ ID NOS:  13

<210> SEQ ID NO 1
<211> LENGTH: 1894
<212> TYPE: DNA
<213> ORGANISM: Homo sapiens
<220> FEATURE:
<221> NAME/KEY: CDS
<222> LOCATION: (416)...(1423)
<223> OTHER INFORMATION: Human JKETS.
```

-continued

```
<400> SEQUENCE: 1
gtctgacttc ctcccagcac attcctgcac tctgccgtgt ccacactgcc ccacagaccc      60
agtcctccaa gctgctgcc agctccctgc aagcccctca ggttgggcct tgccacggtg     120
ccagcaggca gccctgggct gggggtaggg gactccctac aggcacgcag ccctgagacc     180
tcagagggcc accccttgag ggtggccagg cccccagtgg ccaacctgag tgctgcctct     240
gccaccagcc ctgctggccc ctggttccgc tggccccca gatgcctggc tgagacacgc      300
cagtggcctc agctgcccac acctcttccc ggccctgaa gttggcactg cagcagacag     360
ctccctgggc accaggcagc taacagacac agccgccagc ccaaacagca gcggc atg     418
                                                                 Met
                                                                   1 ggc agc gcc agc ccg ggt ctg agc agc gta tcc ccc agc cac ctc ctg       466
Gly Ser Ala Ser Pro Gly Leu Ser Ser Val Ser Pro Ser His Leu Leu
          5                  10                  15 ctg ccc ccc gac acg gtg tcg cgg aca ggc ttg gag aag gcg gca gcg       514
Leu Pro Pro Asp Thr Val Ser Arg Thr Gly Leu Glu Lys Ala Ala Ala
              20                  25                  30 ggg gca gtg ggt ctc gag aga cgg gac tgg agt ccc agt cca ccc gcc       562
Gly Ala Val Gly Leu Glu Arg Arg Asp Trp Ser Pro Ser Pro Pro Ala
 35                  40                  45 acg ccc gag cag ggc ctg tcc gcc ttc tac ctc tcc tac ttt gac atg       610
Thr Pro Glu Gln Gly Leu Ser Ala Phe Tyr Leu Ser Tyr Phe Asp Met
 50                  55                  60                  65 ctg tac cct gag gac agc agc tgg gca gcc aag gcc cct ggg gcc agc       658
Leu Tyr Pro Glu Asp Ser Ser Trp Ala Ala Lys Ala Pro Gly Ala Ser
                  70                  75                  80 agt cgg gag gag cca cct gag gag cct gag cag tgc ccg gtc att gac       706
Ser Arg Glu Glu Pro Pro Glu Glu Pro Glu Gln Cys Pro Val Ile Asp
              85                  90                  95 agc caa gcc cca gcg ggc agc ctg gac ttg gtg ccc ggc ggg ctg acc       754
Ser Gln Ala Pro Ala Gly Ser Leu Asp Leu Val Pro Gly Gly Leu Thr
             100                 105                 110 ttg gag gag cac tcg ctg gag cag gtg cag tcc atg gtg gtg ggc gaa       802
Leu Glu Glu His Ser Leu Glu Gln Val Gln Ser Met Val Val Gly Glu
         115                 120                 125 gtg ctc aag gac atc gag acg gcc tgc aag ctg ctc aac atc acc gca       850
Val Leu Lys Asp Ile Glu Thr Ala Cys Lys Leu Leu Asn Ile Thr Ala
130                 135                 140                 145 gat ccc atg gac tgg agc ccc agc aat gtg cag aag tgg ctc ctg tgg       898
Asp Pro Met Asp Trp Ser Pro Ser Asn Val Gln Lys Trp Leu Leu Trp
                 150                 155                 160 aca gag cac caa tac cgg ctg ccc ccc atg ggc aag gcc ttc cag gag       946
Thr Glu His Gln Tyr Arg Leu Pro Pro Met Gly Lys Ala Phe Gln Glu
             165                 170                 175 ctg gcg ggc aag gag ctg tgc gcc atg tcg gag gag cag ttc cgc cag       994
Leu Ala Gly Lys Glu Leu Cys Ala Met Ser Glu Glu Gln Phe Arg Gln
         180                 185                 190 cgc tcc ccc ctg ggt ggg gat gtg ctg cac gcc cac ctg gac atc tgg      1042
Arg Ser Pro Leu Gly Gly Asp Val Leu His Ala His Leu Asp Ile Trp
     195                 200                 205 aag tca gcg gcc tgg atg aaa gag cgg act tca cct ggg gcg att cac      1090
Lys Ser Ala Ala Trp Met Lys Glu Arg Thr Ser Pro Gly Ala Ile His
210                 215                 220                 225 tac tgt gcc tcg acc agt gag gag agc tgg acc gac agc gag gtg gac      1138
Tyr Cys Ala Ser Thr Ser Glu Glu Ser Trp Thr Asp Ser Glu Val Asp
                 230                 235                 240
```

-continued

| | |
|---|---|
| tca tca tgc tcc ggg cag ccc atc cac ctg tgg cag ttc ctc aag gag<br>Ser Ser Cys Ser Gly Gln Pro Ile His Leu Trp Gln Phe Leu Lys Glu<br>245 250 255 | 1186 |
| ttg cta ctc aag ccc cac agc tat ggc cgc ttc att agg tgg ctc aac<br>Leu Leu Leu Lys Pro His Ser Tyr Gly Arg Phe Ile Arg Trp Leu Asn<br>260 265 270 | 1234 |
| aag gag aag ggc atc ttc aaa att gag gac tca gcc cag gtg gcc cgg<br>Lys Glu Lys Gly Ile Phe Lys Ile Glu Asp Ser Ala Gln Val Ala Arg<br>275 280 285 | 1282 |
| ctg tgg ggc atc cgc aag aac cgt ccc gcc atg aac tac gac aag ctg<br>Leu Trp Gly Ile Arg Lys Asn Arg Pro Ala Met Asn Tyr Asp Lys Leu<br>290 295 300 305 | 1330 |
| agc cgc tcc atc cgc cag tat tac aag aag ggc atc atc cgg aag cca<br>Ser Arg Ser Ile Arg Gln Tyr Tyr Lys Lys Gly Ile Ile Arg Lys Pro<br>310 315 320 | 1378 |
| gac atc tcc cag cgc ctc gtc tac cag ttc gtg cac ccc atc tga<br>Asp Ile Ser Gln Arg Leu Val Tyr Gln Phe Val His Pro Ile *<br>325 330 335 | 1423 |
| gtgcctggcc cagggcctga aacccgcccct caggggcctc tctcctgcct gccctgcctc | 1483 |
| agccaggccc tgagatgggg gaaaacgggc agtctgctct gctgctctga ccttccagag | 1543 |
| cccaaggtca gggaggggca accaactgcc ccagggggat atgggtcctc tggggccttc | 1603 |
| gggaccatgg ggcagggggtg cttcctcctc aggcccagct gctcccctgg aggacagagg | 1663 |
| gagacagggc tgctccccaa cacctgcctc tgaccccagc atttccagag cagagcctac | 1723 |
| agaagggcag tgactcgaca aaggccacag gcagtccagg cctctctctg ctccatcccc | 1783 |
| ctgcctccca ttctgcacca cacctggcat ggtgcaggga gacatctgca cccctgagtt | 1843 |
| gggcagccag gagtgccccc gggaatggat aataaagata ctagagaact g | 1894 |

<210> SEQ ID NO 2
<211> LENGTH: 335
<212> TYPE: PRT
<213> ORGANISM: Homo sapiens

<400> SEQUENCE: 2

Met Gly Ser Ala Ser Pro Gly Leu Ser Ser Val Ser Pro Ser His Leu
1               5                   10                  15

Leu Leu Pro Pro Asp Thr Val Ser Arg Thr Gly Leu Glu Lys Ala Ala
                20                  25                  30

Ala Gly Ala Val Gly Leu Glu Arg Arg Asp Trp Ser Pro Ser Pro Pro
            35                  40                  45

Ala Thr Pro Glu Gln Gly Leu Ser Ala Phe Tyr Leu Ser Tyr Phe Asp
        50                  55                  60

Met Leu Tyr Pro Glu Asp Ser Ser Trp Ala Ala Lys Ala Pro Gly Ala
65                  70                  75                  80

Ser Ser Arg Glu Glu Pro Glu Glu Pro Gln Cys Pro Val Ile
                85                  90                  95

Asp Ser Gln Ala Pro Ala Gly Ser Leu Asp Leu Val Pro Gly Gly Leu
                100                 105                 110

Thr Leu Glu Glu His Ser Leu Glu Gln Val Gln Ser Met Val Val Gly
            115                 120                 125

Glu Val Leu Lys Asp Ile Glu Thr Ala Cys Lys Leu Leu Asn Ile Thr
        130                 135                 140

Ala Asp Pro Met Asp Trp Ser Pro Ser Asn Val Gln Lys Trp Leu Leu
145                 150                 155                 160

-continued

```
Trp Thr Glu His Gln Tyr Arg Leu Pro Pro Met Gly Lys Ala Phe Gln
                165                 170                 175

Glu Leu Ala Gly Lys Glu Leu Cys Ala Met Ser Glu Gln Phe Arg
            180                 185                 190

Gln Arg Ser Pro Leu Gly Gly Asp Val Leu His Ala His Leu Asp Ile
        195                 200                 205

Trp Lys Ser Ala Ala Trp Met Lys Glu Arg Thr Ser Pro Gly Ala Ile
    210                 215                 220

His Tyr Cys Ala Ser Thr Ser Glu Glu Ser Trp Thr Asp Ser Glu Val
225                 230                 235                 240

Asp Ser Ser Cys Ser Gly Gln Pro Ile His Leu Trp Gln Phe Leu Lys
                245                 250                 255

Glu Leu Leu Leu Lys Pro His Ser Tyr Gly Arg Phe Ile Arg Trp Leu
                260                 265                 270

Asn Lys Glu Lys Gly Ile Phe Lys Ile Glu Asp Ser Ala Gln Val Ala
                275                 280                 285

Arg Leu Trp Gly Ile Arg Lys Asn Arg Pro Ala Met Asn Tyr Asp Lys
            290                 295                 300

Leu Ser Arg Ser Ile Arg Gln Tyr Tyr Lys Lys Gly Ile Ile Arg Lys
305                 310                 315                 320

Pro Asp Ile Ser Gln Arg Leu Val Tyr Gln Phe Val His Pro Ile
                325                 330                 335

<210> SEQ ID NO 3
<211> LENGTH: 84
<212> TYPE: PRT
<213> ORGANISM: Homo sapiens
<220> FEATURE:
<221> NAME/KEY: DOMAIN
<222> LOCATION: (1)...(84)
<223> OTHER INFORMATION: Ets domain of JKETS.

<400> SEQUENCE: 3

Ile His Leu Trp Gln Phe Leu Lys Glu Leu Leu Leu Lys Pro His Ser
1               5                   10                  15

Tyr Gly Arg Phe Ile Arg Trp Leu Asn Lys Glu Lys Gly Ile Phe Lys
            20                  25                  30

Ile Glu Asp Ser Ala Gln Val Ala Arg Leu Trp Gly Ile Arg Lys Asn
        35                  40                  45

Arg Pro Ala Met Asn Tyr Asp Lys Leu Ser Arg Ser Ile Arg Gln Tyr
    50                  55                  60

Tyr Lys Lys Gly Ile Ile Arg Lys Pro Asp Ile Ser Gln Arg Leu Val
65                  70                  75                  80

Tyr Gln Phe Val

<210> SEQ ID NO 4
<211> LENGTH: 1907
<212> TYPE: DNA
<213> ORGANISM: Homo sapiens
<220> FEATURE:
<221> NAME/KEY: CDS
<222> LOCATION: (96)...(1211)
<223> OTHER INFORMATION: Human epithelial-restricted with serine box
      (ESX) protein.
```

-continued

```
<400> SEQUENCE: 4
cggccagata cctcagcgct acctggcgga actggatttc tctcccgcct gccggcctgc        60
ctgccacagc cggactccgc cactccggta gcctc atg gct gca acc tgt gag         113
                                      Met Ala Ala Thr Cys Glu
                                       1               5 att agc aac att ttt agc aac tac ttc agt gcg atg tac agc tcg gag        161
Ile Ser Asn Ile Phe Ser Asn Tyr Phe Ser Ala Met Tyr Ser Ser Glu
             10                  15                  20 gac tcc acc ctg gcc tct gtt ccc cct gct gcc acc ttt ggg gcc gat        209
Asp Ser Thr Leu Ala Ser Val Pro Pro Ala Ala Thr Phe Gly Ala Asp
         25                  30                  35 gac ttg gta ctg acc ctg agc aac ccc cag atg tca ttg gag ggt aca        257
Asp Leu Val Leu Thr Leu Ser Asn Pro Gln Met Ser Leu Glu Gly Thr
 40                  45                  50 gag aag gcc agc tgg ttg ggg gaa cag ccc cag ttc tgg tcg aag acg        305
Glu Lys Ala Ser Trp Leu Gly Glu Gln Pro Gln Phe Trp Ser Lys Thr
 55                  60                  65                  70 cag gtt ctg gac tgg atc agc tac caa gtg gag aag aac aag tac gac        353
Gln Val Leu Asp Trp Ile Ser Tyr Gln Val Glu Lys Asn Lys Tyr Asp
                 75                  80                  85 gca agc gcc att gac ttc tca cga tgt gac atg gat ggc gcc acc ctc        401
Ala Ser Ala Ile Asp Phe Ser Arg Cys Asp Met Asp Gly Ala Thr Leu
             90                  95                 100 tgc aat tgt gcc ctt gag gag ctg cgt ctg gtc ttt ggg cct ctg ggg        449
Cys Asn Cys Ala Leu Glu Glu Leu Arg Leu Val Phe Gly Pro Leu Gly
        105                 110                 115 gac caa ctc cat gcc cag ctg cga gac ctc act tcc agc tct tct gat        497
Asp Gln Leu His Ala Gln Leu Arg Asp Leu Thr Ser Ser Ser Ser Asp
    120                 125                 130 gag ctc agt tgg atc att gag ctg ctg gag aag gat ggc atg gcc ttc        545
Glu Leu Ser Trp Ile Ile Glu Leu Leu Glu Lys Asp Gly Met Ala Phe
135                 140                 145                 150 cag gag gcc cta gac cca ggg ccc ttt gac cag ggc agc ccc ttt gcc        593
Gln Glu Ala Leu Asp Pro Gly Pro Phe Asp Gln Gly Ser Pro Phe Ala
                155                 160                 165 cag gag ctg ctg gac gac ggt cag caa gcc agc ccc tac cac ccc ggc        641
Gln Glu Leu Leu Asp Asp Gly Gln Gln Ala Ser Pro Tyr His Pro Gly
            170                 175                 180 agc tgt ggc gca gga gcc ccc tcc cct ggc agc tct gac gtc tcc acc        689
Ser Cys Gly Ala Gly Ala Pro Ser Pro Gly Ser Ser Asp Val Ser Thr
        185                 190                 195 gca ggg act ggt gct tct cgg agc tcc cac tcc tca gac tcc ggt gga        737
Ala Gly Thr Gly Ala Ser Arg Ser Ser His Ser Ser Asp Ser Gly Gly
    200                 205                 210 agt gac gtg gac ctg gat ccc act gat ggc aag ctc ttc ccc agc gat        785
Ser Asp Val Asp Leu Asp Pro Thr Asp Gly Lys Leu Phe Pro Ser Asp
215                 220                 225                 230 ggt ttt cgt gac tgc aag aag ggg gat ccc aag cac ggg aag cgg aaa        833
Gly Phe Arg Asp Cys Lys Lys Gly Asp Pro Lys His Gly Lys Arg Lys
                235                 240                 245 cga ggc cgg ccc cga aag ctg agc aaa gag tac tgg gac tgt ctc gag        881
Arg Gly Arg Pro Arg Lys Leu Ser Lys Glu Tyr Trp Asp Cys Leu Glu
            250                 255                 260 ggc aag aag agc aag cac gcg ccc aga ggc acc cac ctg tgg gag ttc        929
Gly Lys Lys Ser Lys His Ala Pro Arg Gly Thr His Leu Trp Glu Phe
        265                 270                 275 atc cgg gac atc ctc atc cac ccg gag ctc aac gag ggc ctc atg aag        977
Ile Arg Asp Ile Leu Ile His Pro Glu Leu Asn Glu Gly Leu Met Lys
    280                 285                 290
```

```
tgg gag aat cgg cat gaa ggc gtc ttc aag ttc ctg cgc tcc gag gct    1025
Trp Glu Asn Arg His Glu Gly Val Phe Lys Phe Leu Arg Ser Glu Ala
295                 300                 305                 310 gtg gcc caa cta tgg ggc caa aag aaa aag aac agc aac atg acc tac    1073
Val Ala Gln Leu Trp Gly Gln Lys Lys Lys Asn Ser Asn Met Thr Tyr
                315                 320                 325 gag aag ctg agc cgg gcc atg agg tac tac tac aaa cgg gag atc ctg    1121
Glu Lys Leu Ser Arg Ala Met Arg Tyr Tyr Tyr Lys Arg Glu Ile Leu
            330                 335                 340 gaa cgg gtg gat ggc cgg cga ctc gtc tac aag ttt ggc aaa aac tca    1169
Glu Arg Val Asp Gly Arg Arg Leu Val Tyr Lys Phe Gly Lys Asn Ser
        345                 350                 355 agc ggc tgg aag gag gaa gag gtt ctc cag agt cgg aac tga            1211
Ser Gly Trp Lys Glu Glu Glu Val Leu Gln Ser Arg Asn *
    360                 365                 370 gggttggaac tataccggg accaaactca cggaccactc gaggcctgca aaccttcctg   1271
ggaggacagg caggccagat gcccctcca ctggggaatg ctcccagctg tgctgtggag   1331
agaagctgat gttttggtgt attgtcagcc atcgtccttg gactcggaga ctatggcctc   1391
gcctccccac cctcctcttg gaattacaag ccctggggtt tgaagctgac tttatagctg   1451
caagtgtatc tccttttatc tggtgcctcc tcaaacccag tctcagacac ttaaatgcag   1511
acaacacctt cttcctgcag acacttggac tgagccaagg aggcttggga ggccctaggg   1571
agcaccgtga tggagaggac agagcagggg ctccagcact tctttctgga ctggcgttca   1631
cctccctgct cagtgcttgg gctccacggg caggggtcag agcactccct aatttatgtg   1691
ctatataaat atgtcagatg tacatagaga tctattttt ctaaaacatt ccctccca    1751
ctcctctccc acagagtgct ggactgttcc aggccctcca gtgggctgat gctgggaccc   1811
ttaggatggg gctcccagct cctttctcct gtgaatggag gcagagacct ccaataaagt   1871
gccttctggg cttttctaa aaaaaaaaaa aaaaaa                             1907
```

<210> SEQ ID NO 5
<211> LENGTH: 371
<212> TYPE: PRT
<213> ORGANISM: Homo sapiens

<400> SEQUENCE: 5

```
Met Ala Ala Thr Cys Glu Ile Ser Asn Ile Phe Ser Asn Tyr Phe Ser
1               5                   10                  15

Ala Met Tyr Ser Ser Glu Asp Ser Thr Leu Ala Ser Val Pro Pro Ala
            20                  25                  30

Ala Thr Phe Gly Ala Asp Asp Leu Val Leu Thr Leu Ser Asn Pro Gln
        35                  40                  45

Met Ser Leu Glu Gly Thr Glu Lys Ala Ser Trp Leu Gly Glu Gln Pro
    50                  55                  60

Gln Phe Trp Ser Lys Thr Gln Val Leu Asp Trp Ile Ser Tyr Gln Val
65                  70                  75                  80

Glu Lys Asn Lys Tyr Asp Ala Ser Ala Ile Asp Phe Ser Arg Cys Asp
                85                  90                  95

Met Asp Gly Ala Thr Leu Cys Asn Cys Ala Leu Glu Glu Leu Arg Leu
            100                 105                 110

Val Phe Gly Pro Leu Gly Asp Gln Leu His Ala Gln Leu Arg Asp Leu
        115                 120                 125

Thr Ser Ser Ser Asp Glu Leu Ser Trp Ile Ile Glu Leu Leu Glu
    130                 135                 140
```

-continued

```
Lys Asp Gly Met Ala Phe Gln Glu Ala Leu Asp Pro Gly Pro Phe Asp
145                 150                 155                 160

Gln Gly Ser Pro Phe Ala Gln Glu Leu Leu Asp Asp Gly Gln Gln Ala
            165                 170                 175

Ser Pro Tyr His Pro Gly Ser Cys Gly Ala Gly Ala Pro Ser Pro Gly
            180                 185                 190

Ser Ser Asp Val Ser Thr Ala Gly Thr Gly Ala Ser Arg Ser Ser His
            195                 200                 205

Ser Ser Asp Ser Gly Gly Ser Asp Val Asp Leu Asp Pro Thr Asp Gly
            210                 215                 220

Lys Leu Phe Pro Ser Asp Gly Phe Arg Asp Cys Lys Lys Gly Asp Pro
225                 230                 235                 240

Lys His Gly Lys Arg Lys Arg Gly Arg Pro Arg Lys Leu Ser Lys Glu
            245                 250                 255

Tyr Trp Asp Cys Leu Glu Gly Lys Lys Ser Lys His Ala Pro Arg Gly
            260                 265                 270

Thr His Leu Trp Glu Phe Ile Arg Asp Ile Leu Ile His Pro Glu Leu
            275                 280                 285

Asn Glu Gly Leu Met Lys Trp Glu Asn Arg His Glu Gly Val Phe Lys
290                 295                 300

Phe Leu Arg Ser Glu Ala Val Ala Gln Leu Trp Gly Gln Lys Lys Lys
305                 310                 315                 320

Asn Ser Asn Met Thr Tyr Glu Lys Leu Ser Arg Ala Met Arg Tyr Tyr
            325                 330                 335

Tyr Lys Arg Glu Ile Leu Glu Arg Val Asp Gly Arg Arg Leu Val Tyr
            340                 345                 350

Lys Phe Gly Lys Asn Ser Ser Gly Trp Lys Glu Glu Val Leu Gln
            355                 360                 365

Ser Arg Asn
    370

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide based on JKETS C-terminal
      fragment.

<400> SEQUENCE: 6

Arg Lys Pro Asp Ile Ser Gln Arg Leu Val Tyr Gln Phe Val His Pro
1               5                   10                  15

Ile

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide based on ESX C-terminal
      fragment.

<400> SEQUENCE: 7

Gly Lys Asn Ser Ser Gly Trp Lys Glu Glu Val Leu Gln Ser Met
1               5                   10                  15

<210> SEQ ID NO 8
<211> LENGTH: 1751
<212> TYPE: DNA
```

<213> ORGANISM: Homo sapiens
<220> FEATURE:
<221> NAME/KEY: promoter
<222> LOCATION: (1)...(1381)
<223> OTHER INFORMATION: JKETS promoter
<221> NAME/KEY: TATA_signal
<222> LOCATION: (1356)...(1360)
<223> OTHER INFORMATION: TATA box.

<400> SEQUENCE: 8

```
actatagggc acgcgtggtc gacggcccgg gctagtatta atgcatcaga atgctgtgat      60
ataagccagg cttctgtgag agtggggagg agggaggcgt ggccaccaga gaagcaggca     120
caaaaacgca ctctagggga aggagatcca cctggaaacg cagcgtgtct ttctttattg     180
accctggagg gctggaccat tgggattag gagtggtcga gtgtaccatt tcaggacctt     240
gtgttacctc cccttcctcc gctccatcct ccctcaacct tctctgggga atgactgata     300
actgatcctc aaccaagtg ccagtgacga taacagccaa gtacagggct ccctgggggt     360
gcaaagtgca accttacgtt ggagaatgtg ggtattggtg aaggtgaggg gctagttcta     420
aaggccttgg gatccctgc agccccagaa tcctcatgct ctcggcagtt acacagttac     480
tcctgaaaca agagaaaaat cagcattatc tagaactttc tcccgtcaga atggaggtag     540
caggtacgtg gagcccttct gagatgattt ggagaaagga aggcccagcc tccagggaca     600
actctcagcc cacctggcag gacatggagg aagccaaaag ctggactgtg tggcccccgc     660
agggctcaag gaggtggagg gtctgggca gcaagtgctt ggtggtgggt atctctgtcc     720
tgcatggcat ccctgccatc acctttgggg gctatgggag agcaagttgc tgctgactgg     780
cccccgatta caggcctggg aaagcgagct aggagtcctt cctcaccgcc actgtgtgac     840
aggtctgcat gaggaccctg tggggcacag agaacacagt tcccaccagg tcgcggttgg     900
cccacaagcc tcgggatccc tccccagggt tctctgaagc tctctccatc cctggcctga     960
gtagccagac agcacctcct ccaggaagcc ctcaactgat ttccctagtt ggtgcccacc    1020
ctcagtgccc cctcagtcct ccatctgggc atgggtggtt ctggatctcc actgctgctc    1080
acttgtctgt ctctggccct cagctgatcc atcttagaac cccagccctg acccactcg    1140
acgtatctct ggcgccttgc acgtaatatg agctgagtgg ctatgcagca accaatgaac    1200
gagtgaatga gcgagtgaat gaatgagtcc cctagctgtc agggcatgga tcccccagca    1260
aggaggggga gacctgcaag ggttaatcag gagcctgcct gtggtctgag gtaagcaagg    1320
agtgtatttg ttcaggtaaa taaggaagga ttacttataa tgggaaatca ggccctgacc    1380
aactcttcat ctcgcggctg tctgacttcc tcccagcaca ttcctgcact ctgccgtgtc    1440
cacactgccc cacagaccca gtcctccaag cctgctgcca gctccctgca agccctcag    1500
gttgggcctt gccacggtgc cagcaggcag ccctgggctg ggggtagggg actccctaca    1560
ggcacgcagc cctgagacct cagagggcca ccccttgagg gtggccaggc ccccagtgcc    1620
aacctgagtg ctgcctctgc caccagccct gctggcccct ggttccgctg gcccccccaga    1680
tgcctggctg agacacgcca gtggcctcag ctgcccacac ctcttcccgg cccctgaagt    1740
tggcactgca g                                                         1751
```

<210> SEQ ID NO 9
<211> LENGTH: 1380
<212> TYPE: DNA
<213> ORGANISM: Homo sapiens
<220> FEATURE:
<221> NAME/KEY: promoter
<222> LOCATION: (1)...(1381)
<223> OTHER INFORMATION: JKETS promoter.

<400> SEQUENCE: 9

| | | | | | |
|---|---|---|---|---|---|
| gatacagtag | gtgcctgtta | agcagtggtc | attagtatta | atgcatcaga | atgctgtgat | 60 |
| ataagccagg | cttctgtgag | agtggggagg | agggaggcgt | ggccaccaga | gaagcaggca | 120 |
| caaaaacgca | ctctagggga | aggagatcca | cctggaaacg | cagcgtgtct | ttctttattg | 180 |
| accctggagg | gctggaccat | tggggattag | gagtggtcga | gtgtaccatt | tcaggacctt | 240 |
| gtgttacctc | cccttcctcc | gctccatcct | ccctcaacct | tctctgggga | atgactgata | 300 |
| actgatcctc | aaccaaggtg | ccagtgacga | taacagccaa | gtacagggct | ccctgggggt | 360 |
| gcaaagtgca | accttacgtt | ggagaatgtg | ggtattggtg | aaggtgaggg | gctagttcta | 420 |
| aaggccttgg | gatccctgc | agccccagaa | tcctcatgct | ctcggcagtt | acacagttac | 480 |
| tcctgaaaca | agagaaaaat | cagcattatc | tagaactttc | tcccgtcaga | atggaggtag | 540 |
| caggtacgtg | gagcccttct | gagatgattt | ggagaaagga | aggcccagcc | tcagggaca | 600 |
| actctcagcc | cacctggcag | gacatggagg | aagccaaaag | ctggactgtg | tggcccccgc | 660 |
| agggctcaag | gaggtggagg | gtctgggca | gcaagtgctt | ggtggtgggt | atctctgtcc | 720 |
| tgcatggcat | ccctgccatc | accctttggg | gctatgggag | agcaagttgc | tgctgactgg | 780 |
| cccccgatta | caggcctggg | aaagcgagct | aggagtcctt | cctcaccgcc | actgtgtgac | 840 |
| aggtctgcat | gaggaccctg | tggggcacag | agaacacagt | tcccaccagg | tcgcggttgg | 900 |
| cccacaagcc | tcgggatccc | tccccagggt | tctctgaagc | tctctccatc | cctggcctga | 960 |
| gtagccagac | agcacctcct | ccaggaagcc | ctcaactgat | ttccctagtt | ggtgcccacc | 1020 |
| ctcagtgccc | cctcagtcct | ccatctgggc | atgggtggtt | ctggatctcc | actgctgctc | 1080 |
| acttgtctgt | ctctggccct | cagctgatcc | atcttagaac | cccagccctg | gacccactcg | 1140 |
| acgtatctct | ggcgccttgc | acgtaatatg | agctgagtgg | ctatgcagca | accaatgaac | 1200 |
| gagtgaatga | gcgagtgaat | gaatgagtcc | cctagctgtc | agggcatgga | tcccccagca | 1260 |
| aggagggga | gacctgcaag | ggttaatcag | gagcctgcct | gtggtctgag | gtaagcaagg | 1320 |
| agtgtatttg | ttcaggtaaa | taaggaagga | ttacttataa | tgggaaatca | ggccctgacc | 1380 |

<210> SEQ ID NO 10
<211> LENGTH: 31
<212> TYPE: DNA
<213> ORGANISM: PArtificial Sequence
<220> FEATURE:
<223> OTHER INFORMATION: GSEF-specific primer

<400> SEQUENCE: 10
cagggagggg caaccaactg ccccaggggg a                                31

<210> SEQ ID NO 11
<211> LENGTH: 34
<212> TYPE: DNA
<213> ORGANISM: Artificial Sequence
<220> FEATURE:
<223> OTHER INFORMATION: GSEF-specific primer

<400> SEQUENCE: 11
tatctttatt atccattccc gggggcactc ctgg                              34

<210> SEQ ID NO 12
<211> LENGTH: 3317
<212> TYPE: DNA
<213> ORGANISM: Homo sapiens
<220> FEATURE:
<221> NAME/KEY: source
<222> LOCATION: (1)...(3317)
<223> OTHER INFORMATION: GSEF-encoding sequence with promoter
      (Figs. 2A-2B)
<221> NAME/KEY: promoter
<222> LOCATION: (1)...(1380)
<223> OTHER INFORMATION: Promoter
<221> NAME/KEY: CDS
<222> LOCATION: (1815)...(2819)
<223> OTHER INFORMATION: GSEF coding sequence

<400> SEQUENCE: 12

```
gatacagtag gtgcctgtta agcagtggtc attagtatta atgcatcaga atgctgtgat      60
ataagccagg cttctgtgag agtggggagg agggaggcgt ggccaccaga gaagcaggca     120
caaaaacgca ctctagggga aggagatcca cctggaaacg cagcgtgtct ttctttattg     180
accctggagg gctggaccat tgggattag gagtggtcga gtgtaccatt tcaggacctt      240
gtgttacctc cccttcctcc gctccatcct ccctcaacct tctctgggga atgactgata     300
actgatcctc aaccaaggtg ccagtgacga taacagccaa gtacagggct ccctgggggt     360
gcaaagtgca accttacgtt ggagaatgtg ggtattgtg aaggtgaggg gctagttcta      420
aaggccttgg gatcccctgc agccccagaa tcctcatgct ctcggcagtt acacagttac     480
tcctgaaaca agagaaaaat cagcattatc tagaactttc tcccgtcaga atggaggtag     540
caggtacgtg gagcccttct gagatgattt ggagaaagga aggcccagcc tccagggaca     600
actctcagcc cacctggcag gacatggagg aagccaaaag ctggactgtg tggccccgc      660
agggctcaag gaggtggagg gtctgggca gcaagtgctt ggtggtgggt atctctgtcc      720
tgcatggcat ccctgccatc acccttggg gctatgggga agcaagttgc tgctgactgg      780
cccccgatta caggcctggg aaagcgagct aggagtcctt cctcaccgcc actgtgtgac     840
aggtctgcat gaggaccctg tggggcacag agaacacagt tcccaccagg tcgcggttgg     900
cccacaagcc tcgggatccc tccccagggt tctctgaagc tctctccatc cctggcctga     960
gtagccagac agcacctcct ccaggaagcc ctcaactgat ttccctagtt ggtgcccacc    1020
ctcagtgccc cctcagtcct ccatctgggc atgggtggtt ctggatctcc actgctgctc    1080
acttgtctgt ctctggccct cagctgatcc atcttagaac cccagccctg gacccactcg    1140
acgtatctct ggcgccttgc acgtaatatg agctgagtgg ctatgcagca accaatgaac    1200
gagtgaatga gcgagtgaat gaatgagtcc cctagctgtc agggcatgga tcccccagca    1260
aggaggggga gacctgcaag ggttaatcag gagcctgcct gtggtctgag gtaagcaagg    1320
agtgtatttg ttcaggtaaa taaggaagga ttacttataa tggaaatca ggccctgacc     1380
aactcttcat ctcgcggctg tctgacttcc tcccagcaca ttcctgcact ctgccgtgtc    1440
cacactgccc cacagaccca gtcctccaag cctgctgcca gctccctgca agcccctcag    1500
gttgggcctt gccacggtgc cagcaggcag ccctgggctg ggggtagggg actccctaca    1560
ggcacgcagc cctgagacct cagagggcca ccccttgagg gtggccaggc cccagtggc     1620
caacctgagt gctgcctctg ccaccagccc tgctggcccc tggttccgct ggccccccag    1680
atgcctggct gagacacgcc agtggcctca gctgcccaca cctcttcccg gcccctgaag    1740
ttggcactgc agcagacagc tccctgggca ccaggcagct aacagacaca gccgccagcc    1800
```

-continued

| | | |
|---|---|---|
| caaacagcag cggc atg ggc agc gcc agc ccg ggt ctg agc agc gta tcc<br>        Met Gly Ser Ala Ser Pro Gly Leu Ser Ser Val Ser<br>         1               5                  10 | 1850 |
| ccc agc cac ctc ctg ctg ccc ccc gac acg gtg tcg cgg aca ggc ttg<br>Pro Ser His Leu Leu Leu Pro Pro Asp Thr Val Ser Arg Thr Gly Leu<br>         15                  20                  25 | 1898 |
| gag aag gcg gca gcg ggg gca gtg ggt ctc gag aga cgg gac tgg agt<br>Glu Lys Ala Ala Ala Gly Ala Val Gly Leu Glu Arg Arg Asp Trp Ser<br> 30                  35                  40 | 1946 |
| ccc agt cca ccc gcc acg ccc gag cag ggc ctg tcc gcc ttc tac ctc<br>Pro Ser Pro Pro Ala Thr Pro Glu Gln Gly Leu Ser Ala Phe Tyr Leu<br> 45                  50                  55                  60 | 1994 |
| tcc tac ttt gac atg ctg tac cct gag gac agc agc tgg gca gcc aag<br>Ser Tyr Phe Asp Met Leu Tyr Pro Glu Asp Ser Ser Trp Ala Ala Lys<br>                  65                  70                  75 | 2042 |
| gcc cct ggg gcc agc agt cgg gag gag cca cct gag gag cct gag cag<br>Ala Pro Gly Ala Ser Ser Arg Glu Glu Pro Pro Glu Glu Pro Glu Gln<br>                  80                  85                  90 | 2090 |
| tgc ccg gtc att gac agc caa gcc cca gcg ggc agc ctg gac ttg gtg<br>Cys Pro Val Ile Asp Ser Gln Ala Pro Ala Gly Ser Leu Asp Leu Val<br>                  95                 100                 105 | 2138 |
| ccc ggc ggg ctg acc ttg gag gag cac tcg ctg gag cag gtg cag tcc<br>Pro Gly Gly Leu Thr Leu Glu Glu His Ser Leu Glu Gln Val Gln Ser<br>110                 115                 120 | 2186 |
| atg gtg gtg ggc gaa gtg ctc aag gac atc gag acg gcc tgc aag ctg<br>Met Val Val Gly Glu Val Leu Lys Asp Ile Glu Thr Ala Cys Lys Leu<br>125                 130                 135                 140 | 2234 |
| ctc aac atc acc gca gat ccc atg gac tgg agc ccc agc aat gtg cag<br>Leu Asn Ile Thr Ala Asp Pro Met Asp Trp Ser Pro Ser Asn Val Gln<br>                 145                 150                 155 | 2282 |
| aag tgg ctc ctg tgg aca gag cac caa tac cgg ctg ccc ccc atg ggc<br>Lys Trp Leu Leu Trp Thr Glu His Gln Tyr Arg Leu Pro Pro Met Gly<br>                 160                 165                 170 | 2330 |
| aag gcc ttc cag gag ctg gcg ggc aag gag ctg tgc gcc atg tcg gag<br>Lys Ala Phe Gln Glu Leu Ala Gly Lys Glu Leu Cys Ala Met Ser Glu<br>                 175                 180                 185 | 2378 |
| gag cag ttc cgc cag cgc tcg ccc ctg ggt gga gat gtg ctg cac gcc<br>Glu Gln Phe Arg Gln Arg Ser Pro Leu Gly Gly Asp Val Leu His Ala<br>190                 195                 200 | 2426 |
| cac ctg gac atc tgg aag tca gcg gcc tgg atg aaa gag cgg act tca<br>His Leu Asp Ile Trp Lys Ser Ala Ala Trp Met Lys Glu Arg Thr Ser<br>205                 210                 215                 220 | 2474 |
| cct ggg gcg att cac tac tgt gcc tcg acc agt gag gag agc tgg acc<br>Pro Gly Ala Ile His Tyr Cys Ala Ser Thr Ser Glu Glu Ser Trp Thr<br>                 225                 230                 235 | 2522 |
| gac agc gag gtg gac tca tca tgc tcc ggg cag ccc atc cac ctg tgg<br>Asp Ser Glu Val Asp Ser Ser Cys Ser Gly Gln Pro Ile His Leu Trp<br>                 240                 245                 250 | 2570 |
| cag ttc ctc aag gag ttg cta ctc aag ccc cac agc tat ggc cgc ttc<br>Gln Phe Leu Lys Glu Leu Leu Leu Lys Pro His Ser Tyr Gly Arg Phe<br>                 255                 260                 265 | 2618 |
| att agg tgg ctc aac aag gag aag ggc atc ttc aaa att gag gac tca<br>Ile Arg Trp Leu Asn Lys Glu Lys Gly Ile Phe Lys Ile Glu Asp Ser<br> 270                 275                 280 | 2666 |
| gcc cag gtg gcc cgg ctg tgg ggc atc cgc aag aac cgt ccc gcc atg<br>Ala Gln Val Ala Arg Leu Trp Gly Ile Arg Lys Asn Arg Pro Ala Met<br>285                 290                 295                 300 | 2714 |
| aac tac gac aag ctg agc cgc tcc atc cgc cag tat tac aag aag ggc<br>Asn Tyr Asp Lys Leu Ser Arg Ser Ile Arg Gln Tyr Tyr Lys Lys Gly<br>                 305                 310                 315 | 2762 |

```
atc atc cgg aag cca gac atc tcc cag cgc ctc gtc tac cag ttc gtg    2810
Ile Ile Arg Lys Pro Asp Ile Ser Gln Arg Leu Val Tyr Gln Phe Val
        320                 325                 330 cac ccc atc tgagtgcctg gcccagggcc tgaaacccgc cctcaggggc             2859
His Pro Ile
        335 ctctctcctg cctgccctgc ctcagccagg ccctgagatg ggggaaaacg ggcagtctgc   2919 tctgctgctc tgaccttcca gagcccaagg tcagggaggg gcaaccaact gccccagggg   2979 gatatgggtc ctctggggcc ttcgggaccc tggggcaggg gtgcttcctc ctcaggccca   3039 gctgctcccc tggaggacag agggagacag ggctgctccc caacacctgc ctctgacccc   3099 agcatttcca gagcagagcc tacagaaggg cagtgactcg acaaaggcca caggcagtcc   3159 aggcctctct ctgctccatc ccctgcctc ccattctgca ccacacctgg catggtgcag    3219 ggagacatct gcaccctga gttgggcagc caggagtgcc cccgggaatg gataatagag    3279 atactagaga actgaaaaaa aaaaaaaaaa aaaaaaa                            3317
```

<210> SEQ ID NO 13
<211> LENGTH: 335
<212> TYPE: PRT
<213> ORGANISM: Homo sapiens

<400> SEQUENCE: 13

```
Met Gly Ser Ala Ser Pro Gly Leu Ser Val Ser Pro Ser His Leu
1               5                   10                  15

Leu Leu Pro Pro Asp Thr Val Ser Arg Thr Gly Leu Glu Lys Ala Ala
                20                  25                  30

Ala Gly Ala Val Gly Leu Glu Arg Arg Asp Trp Ser Pro Ser Pro
            35                  40                  45

Ala Thr Pro Glu Gln Gly Leu Ser Ala Phe Tyr Leu Ser Tyr Phe Asp
        50                  55                  60

Met Leu Tyr Pro Glu Asp Ser Ser Trp Ala Ala Lys Ala Pro Gly Ala
65                  70                  75                  80

Ser Ser Arg Glu Glu Pro Pro Glu Glu Pro Gln Cys Pro Val Ile
                85                  90                  95

Asp Ser Gln Ala Pro Ala Gly Ser Leu Asp Leu Val Pro Gly Gly Leu
            100                 105                 110

Thr Leu Glu Glu His Ser Leu Glu Gln Val Gln Ser Met Val Val Gly
        115                 120                 125

Glu Val Leu Lys Asp Ile Glu Thr Ala Cys Lys Leu Leu Asn Ile Thr
    130                 135                 140

Ala Asp Pro Met Asp Trp Ser Pro Ser Asn Val Gln Lys Trp Leu Leu
145                 150                 155                 160

Trp Thr Glu His Gln Tyr Arg Leu Pro Pro Met Gly Lys Ala Phe Gln
                165                 170                 175

Glu Leu Ala Gly Lys Glu Leu Cys Ala Met Ser Glu Glu Gln Phe Arg
            180                 185                 190

Gln Arg Ser Pro Leu Gly Gly Asp Val Leu His Ala His Leu Asp Ile
        195                 200                 205

Trp Lys Ser Ala Ala Trp Met Lys Glu Arg Thr Ser Pro Gly Ala Ile
    210                 215                 220

His Tyr Cys Ala Ser Thr Ser Glu Glu Ser Trp Thr Asp Ser Glu Val
225                 230                 235                 240

Asp Ser Ser Cys Ser Gly Gln Pro Ile His Leu Trp Gln Phe Leu Lys
                245                 250                 255
```

```
-continued

Glu Leu Leu Leu Lys Pro His Ser Tyr Gly Arg Phe Ile Arg Trp Leu
            260                 265                 270

Asn Lys Glu Lys Gly Ile Phe Lys Ile Glu Asp Ser Ala Gln Val Ala
        275                 280                 285

Arg Leu Trp Gly Ile Arg Lys Asn Arg Pro Ala Met Asn Tyr Asp Lys
        290                 295                 300

Leu Ser Arg Ser Ile Arg Gln Tyr Tyr Lys Lys Gly Ile Ile Arg Lys
305                 310                 315                 320

Pro Asp Ile Ser Gln Arg Leu Val Tyr Gln Phe Val His Pro Ile
                325                 330                 335
```

METHODS FOR DETERMINING METASTATIC POTENTIAL OF BREAST CANCER CELLS BY DETECTING GSEF GENE PRODUCT EXPRESSION

CROSS REFERENCE TO RELATED APPLICATIONS

This application claims the benefit of prior U.S. Priovisional Application No. 60/134,112, filed May 14, 1999, which application is incorporated herein by reference.

FIELD OF THE INVENTION

This invention relates generally to identification of markers and therapeutic targets in breast cancer.

INTRODUCTION

1. Background

Breast cancer is one of the most common malignant diseases with about a million new cases per year worldwide. Despite use of a number of histochemical, genetic, and immunological markers, clinicians still have a difficult time predicting which tumors will metastasize to other organs. Some patients are in need of adjuvant therapy to prevent recurrence and metastasis and others are not. However, distinguishing between these subpopulations of patients is not straightforward, and course of treatment is not easily charted. There is a need in the art for new markers for distinguishing between tumors which will or have metastasized and those which are less likely to metastasize.

The majority of epithelial cancers originate due to altered gene expression leading to defects in cell differentiation and proliferation. One major mechanism of metastasis in breast carcinomas seems to be the so-called epithelial to mesenchymal transition (EMT) observed in invasive embryonic epithelia (Hendrix (1997) Am. J. Pathol. 150: 483–495; Pulyaeva (1997) Clin. Exp. Metastasis 15:111–120; McCormick (1989) Cancer Research 49: 4258–4263; Birchmeier (1996) Acta Anat. 156:217–226). One landmark of the EMT is the observation that human breast carcinoma (HBC) cell lines expressing the mesenchymal intermediate filament protein vimentin (VIM+) are highly invasive. (e.g. MDA-MB-231, MDA-MB435 Hendrix (1997) Am. J. Pathol. 150: 483–495) whereas VIM negative cell lines (e.g. MCF-7, MDA-MB-468, MDA-MB-361)) are poorly invasive in nude mice. However, the identity of the regulators of EMT have remained largely unknown.

Prostate cancer is another cancer of considerable importance and in need of additional therapies and diagnostics. Prostate cancer is the most frequent solid cancer in older men and is a major cause of cancer-related death. Initially, prostate cancer involves androgen-dependent proliferation and differentiation of normal prostate basal cells of the prostate epithelia into secretory luminal epithelial cells; however, prostate cancer cells, ultimately become androgen-independent and resistant to hormone therapy. The prostate-specific antigen (PSA) gene has been used as a diagnostic indicator for androgen-independent and androgen-dependent prostate cancer (Ablin (1997) i J. Cancer Res. Clin. Oncol. 123:583–594). Expression of PSA in normal and cancerous luminal epithelial cells of the prostate is under the control of androgens acting through the androgen receptor. Thus, androgen independent prostate cancer generally exhibit decreased PSA expression. Unfortunately, PSA is expressed at least to some degree even in hormone-refractory prostate cancers, indicating that regulation of PSA expression involves an androgen-independent component as well (Sadar (1999) J. Biol. Chem. 274:7777–7783).

The ETS domain, which facilitates DNA binding, is the hallmark of a family of eukaryotic transcription factors. Members of the ETS domain family were originally identified on the basis of a region of primary sequence homology with the protein product of the v-ets oncogene encoded by the E26 avian erythroblastosis virus. ETS-domain transcription factors can be further subclassified primarily because of the high amino acid conservation in their ETS-domain, as well as the conservation of other domains or motifs, e.g., other sequences that can modulate the biological specificity of the protein. The ETS DNA binding domain is also conserved at the structural level, and is a divergent member of the winged helix-turn-helix superfamily of DNA binding proteins.

ETS-domain proteins act either as transcription activators or repressors, which activities are often regulated by signal transduction pathways such as the MAP kinase pathways. Many of the ETS-domain proteins are targeted to promoters by a combination of specific DNA-protein and protein-protein interactions. Many ETS-domain proteins are targets of signal transduction pathways, and are activated in response to various extracellular stimuli. Ets genes and their encoded proteins are involved in a variety of essential biological processes including cell proliferation and differentiation during embryonic development and in the adult. For a review of the ETS-domain transcription factor family, see, e.g., Sharrocks et al. (1997) Int. J. Biochem. Cell Biol. 29:1371–87.

In addition to their roles in developmental pathways, ETS-domain transcription factors have also been implicated in tumorigenesis. For example, a single ETS-related transcription factor, E1AF confers an invasive phenotype upon human cancer cells (Kaya et al. (1996) Oncogene 12:221–7). The role of E1AF as an activator of tumorigenesis is further supported by the finding that transfection of antisense E1AF into oral squamous cell carcinoma cells inhibits tumor invasion by down-regulating matrix metalloproteinase (MMP) genes, which are implicated in invasion and metastasis of tumor cells (Hilda et al. (1997) Oral Oncol. 33(6):426–30). Moreover, expression of E1AF in the non-metastatic cell line MCF-7, an adenocarcinoma; of mammary breast, confers an invasive phenotype upon this cell line. (Kaya et al., 1996, supra)

Other ETS-domain containing proteins have also been implicated in tumorigenesis. For example, the Ets-1 and Ets-2 transcription factors, activate the promoter for invasion-associated urokinase and collagenase genes in response to epidermal growth factor (Watabe et al. (1998) Int J Cancer. 77:128–37). Furthermore, a putative ETS-related transcription factor interacts with a ras-activated enhancer in the mouse osteopontin promoter, a promoter whose expression correlates with the metastatic potential of cells (Guo et al. (1995) Mol Cell Biol 15:476–87).

Although several ETS-domain proteins have been identified (see, e.g., GenBank Accession No. AF071538), their precise biological roles, e.g., the role of such genes in oncogenesis, have not been identified. The present invention identifies the association of expression of one such ETS-domain protein with development of the metastatic phenotype.

Literature

The full-length DNA and amino acid sequences of human PDEF is described in GenBank Accession No. AF071538, and is entitled "Isolation and characterization of a novel prostate epithelium-specific Ets transcription factor, PDEF."

Transfer of the metastatic phenotype by somatic cell fusion with the highly metastatic amelanotic C8161 human melanoma line is described by Barsky et al. (1997) "Evidence of a dominant transcriptional pathway which regulates an undifferentiated and complete metastatic phenotype." *Oncogene* 15:2077–91.

Evidence suggesting malignant melanoma metastasis-regulatory gene may be on human chromosome 6 is described Welch et al. (1994) "Microcell-mediated transfer of chromosome 6 into metastatic human C8161 melanoma cells suppresses metastasis but does not inhibit tumorigenicity," *Oncogene* 9:255–62. Loss of heterozygosity on the long arm of chromosome 6 in breast cancer is described in Noviello et al. (1996) "Loss of heterozygosity on the long arm of chromosome 6 in breast cancer: possibly four regions of deletion." *Clin Cancer Res.* 2:1601–6. Suppression of human melanoma metastasis by introduction of chromosome 6 is described in You et al. (1995) "Suppression of human melanoma metastasis by introduction of chromosome 6 may be partially due to inhibition of motility, but not to inhibition of invasion." *Biochem Biophys Res Commun.* 208:476–84; and Miele et al. (1997) "Suppression of human melanoma metastasis following introduction of chromosome 6 is independent of NME1 (Nm23)." *Clin Exp Metastasis.* 15:259–65.

For a review of the ETS-domain transcription factor family, see Sharrocks et al. (1997) "The ETS-domain transcription factor family," *Int. J. Biochem. Cell Biol.* 29:1371–87.

The full-length DNA and amino acid sequences of human ESX (SEQ ID NOS:4 and 5) are described in Chang et al. (1997) "ESX: a structurally unique Ets overexpressed early during human breast tumorigenesis," *Oncogene* 14:1617–22 and GenBank accession no. U66894.

SUMMARY OF THE INVENTION

The invention features methods for detection of metastatic and potentially metastatic cancerous cells by detection of expression of a gland-specific Ets transcription factor (GSEF) sequence, which encodes an Ets-domain containing protein. The invention also features methods and compositions for modulation of the polypeptide and/or gene activity for prophylactic and therapeutic purposes, such as inhibition of progression of a cell to a metastatic cancerous cell.

It is a primary object of the invention to facilitate identification of cells that are of low metastatic potential (due to expression of GSEF) or high metastatic potential (due to absence of GSEF expression in a cell known to be cancerous).

One advantage of the invention is that detection of GSEF provides for sensitive and accurate detection of cells that are of high metastatic potential, and further provides for distinguishing high metastatic potential cells from low metastatic potential or non metastatic cells.

Additional objects and advantages will be readily apparent to the ordinarily skilled artisan upon reading the instant specification. Including a human GSEF promoter fragment specific for glandular epithelium of secretory glands (including prostate and breast) useful for gene theapie and the development of cancer mouse models.

BRIEF DESCRIPTION OF THE DRAWINGS

FIG. 1 is a photograph of a Western blot analysis of nine human breast carcinoma (HBC) cell lines with high metastatic potential (MDA-MB-435, MDA-MB-231, and ALAB), low metastatic potential or that are nonmetastatic (MDA-MB-468, MDA-MB-361, ZR-75-1, MCF-7, MDA-MB-453, SK-BR-3) as determined by xenographic injection in nude mice. The metastatic phenotype (Met-Phenotyp), the ability to form primary tumors following injection in an animal model (Primary Tumor), and expression of the estrogen receptor (Estrogen Rec) are indicated beneath the photograph.

FIGS. 2A–2B are schematics showing the nucleotide sequence of GSEF cDNA and 5'promoter region. In FIG. 2A, the promoter region is shown relative to the cDNA. The TATA-box and the putative transcription start (+1) are indicated. Potential ETS transcription factor binding sites are shown in bold letters. In FIG. 2B, the coding and 3' noncoding sequence of human GSEF with deduced amino acid sequence are shown. The C-terminal ETS domain is indicated in bold letters. The full-length cDNA-with promoter is provided in the Sequence Listing as SEQ ID NO:12, with the encoded amino acid sequence provided as SEQ ID NO:13.

FIG. 6 is a photograph of a Western blot using specific antisera for the indicated ETS transcription factors. Specific signals are indicated by arrows.

FIG. 11 is a photograph showing the effect of GSEF or E1AF expression upon the morphology of MDA-MB-435 cells.

FIG. 12 is a photograph showing the effect of expression of E1AF or GSEF upon anchorage independent growth of MDA-MB-435 cells.

FIG. 13 is a photograph showing the effect of expression of E1AF or GSEF upon invasiveness of MDA-MB-435 cells in a MATRIGEL™ assay.

DETAILED DESCRIPTION OF THE INVENTION

Figure 3:
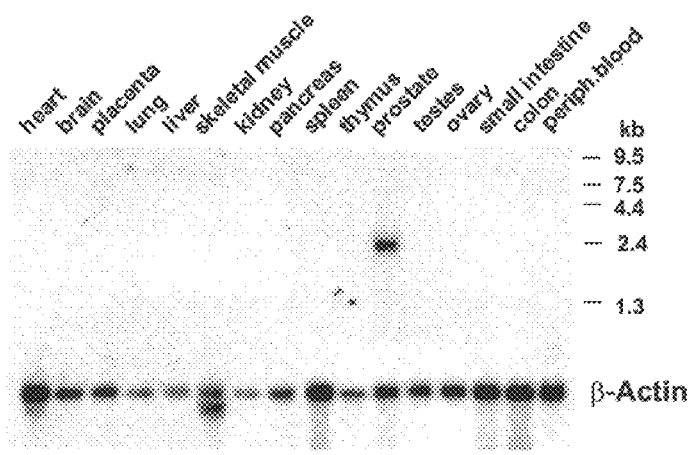
FIG. 3 is a photograph of an RNA blot showing expression of GSEF in a variety of tissues. C7=prostate; D7=salivary gland; D8=mammary gland; C8=stomach; C4=colon; F3=trachea; H3 and H4=positive controls.

Before the present invention is described, it is to be understood that this invention is not limited to any particular embodiment described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms, "a", "and", and "the" include plural referents unless the context clearly dictates otherwise. Thus, for example, reference to "a cell" includes a plurality of such cells and reference to "the polypeptide" includes reference to one or more polypeptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

OVERVIEW

The present invention is based on the discovery that expression of the gene encoding GSEF (previously referred to as JKETS), an ETS-domain-containing protein is decreased in cells of high metastatic potential relative to cells of either low metastatic potential cells, non-metastatic, cancerous cells, or normal cells. This finding indicates that GSEF is a tumor suppressor gene, and that inhibition of GSEF function (e.g., by inhibition of gene expression, alteration in the GSEF polypeptide biological activity, etc.) leads to development of the metastatic phenotype.

Nucleic acid compositions encoding GSEF polypeptides or fragments thereof are thus useful in, for example, producing or identifying compositions that modulate the expression or function of the encoded proteins; in identifying homologous or related genes; for gene therapy; mapping functional regions of the proteins; and in studying associated physiological pathways.

Characterization of GSEF

The GSEF nucleotide and amino acid sequences are provided herein as SEQ ID NOS:1 and 2, respectively. The GSEF cDNA sequence comprising the GSEF promoter and coding sequence are provided as SEQ ID NO:12, with the encoded GSEF amino acid sequence provided again as SEQ ID NO:13. The functional domains and other features of GSEF, are described in detail below.

GSEF Nucleic Acid Compositions

Nucleic acids encoding the GSEF of the invention may be cDNA, genomic DNA, the corresponding RNA, or a fragment thereof. The term "GSEF gene" shall be intended to mean the open reading frame encoding any of the provided GSEF polypeptides (with the GSEF polypeptide of SEQ ID NO:2 being of particular interest), introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome. The term "nucleic acid" is meant to encompass, but is not necessarily limited to, DNA, cDNA, genomic DNA, and RNA compositions. Where a specific DNA sequence is referred to, the sequence is understood to encompass both the DNA and its corresponding RNA, unless specifically noted otherwise.

The GSEF-encoding polynucleotides are isolated and obtained in substantial purity, generally as other than an intact chromosome. Usually, the DNA will be obtained substantially free of other nucleic acid sequences that do not include a GSEF sequence or fragment thereof, generally being at least about 50%, usually at least about 90% pure and are typically "recombinant", i.e. flanked by one or more nucleotides with which it is not normally associated on a naturally occurring chromosome. Of particular interest is a DNA encoding a GSEF.

The subject nucleic acids may be DNA, cDNA, genomic DNA, or RNA corresponding to the subject DNA, cDNA, or genomic DNA sequences, as well as fragments of the subject nucleic acids, particularly fragments that encode a biologically active gene product and/or are useful in the methods disclosed herein (e.g., production of antigenic polypeptides for antibody production, antisense, primers, etc.). Double or single stranded fragments of the DNA sequence may be obtained by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt. Such small DNA fragments are useful as primers for PCR, hybridization screening probes, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The term a as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, removed by nuclear RNA splicing, to create a continuous open reading frame encoding a GSEF protein.

GSEF genes can also be provided as genomic sequences. An exemplary genomic sequence of interest comprises the nucleic acid present between the initiation codon and the stop codon, as defined in the listed sequences, including, all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the invention can be used in a variety of ways as will be readily appreciated by the ordinarily skilled artisan upon disclosure of the nucleic acid compositions described herein. For example, the sequence of the 5' flanking region of the genomic sequence may be utilized for promoter elements, including enhancer binding sites, that provide for tissue-specific and/or developmental regulation in tissues where GSEF genes are expressed. The tissue specific expression is useful for determining the pattern of expression, and for providing promoters that mimic the native pattern of expression (e.g., GSEF). In one embodiment, the GSEF promoter is used to direct expression of genes to normal cells or pre-metastatic cells, particularly breast ductal cells.

Naturally occurring polymorphisms in the promoter regions are useful for determining natural variations in expression, particularly those that may be associated with disease. Alternatively, mutations may be introduced into the promoter regions to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol. Med.* 1: 194–205; Mortlock et al. (1996) *Genome Res.* 6: 327–33; and Joulin and Richard-Foy (1995) *Eur. J. Biochem.* 232: 620–626.

The regulatory sequences may be used to identify cis acting sequences required for transcriptional or translational regulation of GSEF expression, especially in different tissues or stages of development of cancer (e.g., pre-metastatic or normal cells), and to identify cis acting sequences and trans acting factors that regulate or mediate GSEF expression. Such transcription or translational control regions may be operably linked to a GSEF-encoding gene in order to promote expression of wild type or altered GSEF polypeptides or other proteins of interest in cultured cells, or in embryonic, fetal or adult tissues, and for gene therapy.

The DNA may also be used to identify expression of the gene in a biological specimen. The manner in which one probes cells for the presence of particular nucleotide sequences, as genomic DNA or RNA, is well established in the literature and does not require elaboration here. DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of GSEF gene expression in the sample.

Variants, Homologs, and Orthologs

In addition to the specific GSEF sequence provided, GSEF nucleic acid compositions also include nucleic acid sequences having substantial sequence similarity or sequence identity to the specific polynucleotide sequences provided herein. Sequence similarity is calculated based on a reference sequence, which may be a subset of a larger sequence, such as a conserved motif, coding region, flanking region, etc. A reference sequence will usually be at least about 18 contiguous nt long, more usually at least about 30 contiguous nt to about 100 to about 200 contiguous nt long, and may extend to the complete sequence that is being compared. Algorithms for sequence analysis are known in the art, such as BLAST, described in Altschul et al. (1990), *J. Mol. Biol.* 215:403–10. In general, variants of the invention have a sequence identity greater than at least about 65%, preferably at least about 75%, more preferably at least about 85%, and may be greater than at least about 90% or more as determined by the Smith-Waterman homology search algorithm as implemented in MPSRCH program (Oxford Molecular). Exemplary search parameters for use with the MPSRCH program in order to identify sequences of a desired sequence identity are as follows: gap open penalty: 12; and gap extension penalty: 1.

The GSEF nucleic acid compositions discussed herein also encompass naturally-occurring, synthetic, and recombinant variants of the nucleotide sequences (e.g., degenerate variants, allelic variants, etc.). Allelic variants of the polynucleotides of the invention are identified by hybridization of putative allelic variants with nucleotide sequences disclosed herein under stringent conditions. For example, by using the following wash conditions—2×SSC, 0.1% SDS, room temperature twice, 30 minutes each; then 2×SSC, 0.1% SDS, 50° C. once, 30 minutes; then 2×SSC, room temperature twice, 10 minutes each-allelic variants of the polynucleotides of the invention can be identified which contain at most about 25–30% base pair mismatches. In general, allelic variants contain about 15 to 25% base pair mismatches, and may contain as little as about 5–15%, or 2–5%, or 1–2% base pair mismatches, as well as a single base-pair mismatch.

The GSEF nucleic acid compositions also include homologs corresponding to the polynucleotides of the subject invention, where the source of homologous genes may be any mammalian species, e.g., primate species, particularly human; rodents, such as rats, canines, felines, bovines, ovines, equines, yeast, nematodes, etc. Between mammalian species, e.g., human and mouse, homologs have substantial sequence similarity, e.g. at least 75% sequence identity, usually at least 90%, more usually at least 95% between nucleotide sequences.

Modified GSEF-Encoding Nucleic Acid

The nucleic acid compositions of the subject invention also encompass modified GSEF-encoding polynucleotides including, but not necessarily limited to, fragments (e.g., encoding all or a part of the subject polypeptides), polynucleotides encoding genetically modified GSEF polypeptides, etc, with modified GSEF-encoding polynucleotides being of particular interest. The sequences of the GSEF-encoding genes, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

When generating the modified GSEF polypeptides and nucleic acids of the invention, the ordinarily skilled artisan will readily appreciate that she can be guided in her selection of amino acid residues to alter or maintain in view of the knowledge surrounding the structure and function of GSEF. For example, modified GSEF can contain a modification within, and/or contain a modification outside of, a conserved region of the GSEF polypeptide-encoding region, e.g., the ETS-domain. The amino acid sequence of the ETS-domain of GSEF is:

IHLWQFLKELLLKPHSYGRFIRWLNKEKGIFKIE-
DSAQVARLWGIRKNRPAMNYDKLSRSIRQ-
YYKKGIIRKPDISQRLVYQFV (SEQ ID NO:3).

Techniques for in vitro mutagenesis of cloned genes are known. Examples of protocols for site specific mutagenesis may be found in Gustin et al., *Biotechniques* 14:22 (1993); Barany, *Gene* 37:111–23 (1985); Colicelli et al., *Mol Gen Genet* 199–537–9 (1985); and Prentki et al., *Gene* 29:303–13 (1984). Methods for site specific mutagenesis can be found in Sambrook et al., *Molecular Cloning: A Laboratory Manual*, CSH Press 1989, pp. 15.3–15.108; Weiner et al., *Gene* 126:35–41 (1993); Sayers et al., *Biotechniques* 13:592–6 (1992); Jones and Winistorfer, *Biotechniques* 12:528–30 (1992) Barton et al., *Nucleic Acids Res* 18:7349–55 (1990); Marotti and Tomich, *Gene Anal Tech* 6:67–70 (1989); and Zhu, *Anal Biochem* 177:120–4 (1989). Such mutated genes may be used to study structure-function relationships of GSEF genes, particularly to study the differential expression of GSEF in various tissues or to alter properties of these proteins that affect their function or regulation.

GSEF Polypeptides

GSEF nucleic acid sequences may be used to produce all or portions of GSEF polypeptides. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a GSEF-encoding gene (e.g., native to a GSEF-encoding gene), or may be derived from exogenous sources.

The polypeptide may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the GSEF gene (e.g., a GSEF gene) in eukaryotic cells, where the recombinant protein will benefit from native-folding and post-translational modifications. Small peptides can also be synthesized in the laboratory. Peptides that are subsets of a complete GSEF (e.g, GSEF) sequence may be used to identify and investigate parts of the protein important for function, or to raise antibodies directed against these regions.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

The expressed GSEF polypeptides are useful for the production of antibodies, where short fragments provide for antibodies specific for the particular polypeptide, and larger fragments or the entire protein allow for the production of antibodies over the surface of the polypeptide. Antibodies may be raised to the wild-type or variant forms of GSEF polypeptides or immunogenic fragments thereof, or may be raised to isolated peptides corresponding to specific domains, or to the native protein. Antibodies that specifically bind a GSEF polypeptide are of particular interest, particularly antibodies that preferentially bind a GSEF polypeptide (e.g., antibodies that preferentially bind human GSEF polypeptides relative to other ETS-domain family proteins).

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

DIAGNOSTIC APPLICATIONS

The subject nucleic acid and/or polypeptide compositions may be used in a variety of diagnostic applications. Exemplary embodiments of such diagnostic applications are described below.

Diagnosis and Prognosis of Cancer by Detection of GSEF Expression and/or Expression Levels As noted above, the present invention is based on the discovery that GSEF expression is decreased in cells of high metastatic potential relative to cells of low metastatic potential, cells of non-metastatic potential, and to normal cells. In general, the terms "high metastatic potential" and "low metastatic potential" are used to describe the relative ability of a cell to give rise to metastases in an animal model, with "high metastatic potential" cells giving rise to a larger number of metastases and/or larger metastases than "low metastatic potential" cells. Thus, a cell of high metastatic potential poses a greater risk of metastases to the subject than a cell of low metastatic potential. "Non-metastatic cells" are those cells that are cancerous, but that do not develop detectable metastases following injection in an animal model. Exemplary high metastatic potential cells include MDA-MB435, MDA-MB-231, and ALAB. Exemplary low metastatic potential cells include MDA-MB-468, MDA-MB-361, ZR-75-1, and MCF-7.

The invention thus features methods and compositions for diagnosis and prognosis, as well as grading and staging of cancers, by detection of GSEF expression in a biological test sample, e.g, cell sample or tissue sample. The methods of the invention can also be used to monitor patients having a predisposition to develop a particular cancer, e.g., through inheritance of an allele associated with susceptibility to a cancer (e.g., BRCA1, BRCA2, TP53, ATM, or APC for breast cancer). Detection and monitoring of GSEF expression levels can be used to detect potentially malignant events at a molecular level before they are detectable at a gross morphological level.

In general, diagnosis, prognosis, and grading and/or staging of cancers may be performed by a number of methods to determine the relative level of expression of the differentially expressed GSEF gene at the transcriptional level, and/or the absence or presence or altered amounts of a normal or abnormal GSEF polypeptide in patient cells. As used herein, "differentially expressed gene" is intended to refer to a gene having an expression level (e.g., which in turn is associated with a level of GSEF polypeptide production and/or GSEF transcription) that is associated with a decrease in expression level of at least about 25%, usually at least about 50% to 75%, more usually at least about 90% or more. In general, such a decrease in differentially expressed GSEF is indicative of the onset or development of the metastatic phenotype "Diagnosis" as used herein generally includes determination of a subject's susceptibility to a disease or disorder, determination as to whether a subject is unaffected, susceptible to, or presently affected by a disease or disorder, and/or to identify a tumor as benign, non-cancerous, or cancerous (e.g., non-metastatic or metastatic, e.g., high metastatic potential or low metastatic potential). "Prognosis" is used herein to generally mean a determination of the severity of disease (e.g., identification or pre-metastatic or metastatic cancerous states, stages of cancer, etc.), which in turn can be correlated with the potential outcome, response to therapy, etc. A complete diagnosis thus can include diagnosis as discussed above, as well as determination of prognosis, cancer staging, and tumor grading. The present invention particularly encompasses diagnosis and prognosis of subjects in the context of cancers of various origins, particularly breast cancer (e.g., carcinoma in situ (e.g., ductal carcinoma in situ), estrogen receptor (ER)-positive breast cancer, ER-negative breast cancer, or other forms and/or stages of breast cancer) and prostate cancer.

As noted above, detection of GSEF expression levels can be used to determine the stage of the tumor and/or to determine the grade of the tumor, e.g., to determine the differentiation status of the cells of a tumor. Staging, is a process used by physicians to describe how advanced the cancerous state is in a patient. Staging assists the physician in determining a prognosis, planning treatment and evaluating the results of such treatment. Different staging systems are used for different types of cancer, but each generally involves the following determinations: the type of tumor, indicated by T; whether the cancer has metastasized to nearby lymph nodes, indicated by N; and whether the cancer has metastasized to more distant parts of the body, indicated by M. This system of staging is called the TNM system. Generally, if a cancer is only detectable in the area of the primary lesion without having spread to any lymph nodes it is called Stage I. If it has spread only to the closest lymph nodes, it is called Stage II. In Stage III, the cancer has generally spread to the lymph nodes in near proximity to the site of the primary lesion. Cancers that have spread to a distant part of the body, such as the liver, bone, brain or another site, are called Stage IV, the most advanced stage.

Detection of GSEF expression levels can facilitate fine-tuning of the staging process by serving as identifying marker for the aggressiveness of a cancer, e.g. the metastatic potential, as well as the presence in different areas of the body. Thus, a Stage II cancer with a decreased or undetectable GSEF gene product expression level signifying a high metastatic potential cancer can be used to more accurately classify a Stage II tumor as a Stage III tumor, justifying more aggressive therapy. Conversely, higher or normal GSEF gene product expression levels signifying a lower metastatic potential can facilitate staging of a tumor as less aggressive.

The "grade" of a cancer is used to describe how closely a tumor resembles normal tissue of its same type. Based on the microscopic appearance of a tumor, pathologists identify the grade of a tumor based on parameters such as cell morphology, cellular organization, and other markers of differentiation. As a general rule, the grade of a tumor corresponds to its rate of growth or aggressiveness. That is, undifferentiated or high-grade tumors grow more quickly than well differentiated or low-grade tumors. Information about tumor grade is useful in planning treatment and predicting prognosis.

The American Joint Commission on Cancer has recommended the following guidelines for grading tumors: 1) GX Grade cannot be assessed; 2) G1 Well differentiated; G2 Moderately well differentiated; 3) G3 Poorly differentiated; 4) G4 Undifferentiated. Although grading is used by pathologists to describe most cancers, it plays a more important role in treatment planning for certain types than for others. An example is the Gleason system that is specific for prostate cancer, which uses grade numbers to describe the degree of differentiation. Lower Gleason scores indicate well differentiated cells. Intermediate scores denote tumors with moderately differentiated cells. Higher scores describe poorly differentiated cells. Grade is also important in some types of brain tumors and soft tissue sarcomas.

"Gene product" as used in connection with the diagnostic, prognostic, grading, and staging methods of the invention is meant to encompass partial or full-length polypeptides, or mRNA. Detection of the mRNA gene product can involve production of cDNA from the mRNA, and detection of the corresponding cDNA so produced.

"Sample" or "biological sample" as used throughout here are generally meant to refer to samples of biological fluids or tissues, particularly samples obtained from tissues, especially from cells of the type associated with the disease for which the diagnostic application is designed (e.g., ductal adenocarcinoma), and the like. "Samples" is also meant to encompass derivatives and fractions of such samples (e.g., cell lysates). Where the sample is solid tissue, the cells of the tissue can be dissociated or tissue sections can be analyzed.

Methods of the subject invention useful in diagnosis or prognosis typically involve comparison of the amount of GSEF gene product in a sample of interest with that of a control to detect relative differences in the expression of the gene product, where the difference can be measured qualitatively and/or quantitatively. Quantitation can be accomplished, for example, by comparing the level of expression product detected in the sample with the amounts of product present in a standard curve. A comparison can be made visually using ELISA to detect relative amounts of GSEF polypeptides in test and control samples; by using a technique such as densitometry, with or without computerized assistance, to detect relative amounts of detectably labeled GSEF polypeptides or GSEF-encoding nucleic acid; by preparing a representative library of cDNA clones of mRNA isolated from a test sample, sequencing the clones in the library to determine that number of cDNA clones corresponding to the same gene product, and analyzing the number of clones corresponding to that same gene product relative to the number of clones of the same gene product in a control sample; or by using an array to detect relative levels of anti-GSEF polypeptide antibody binding, or to detect relative levels of hybridization to a GSEF-encoding nucleic acid sequences, and comparing the pattern of antibody binding or nucleic acid hybridization to that of a control.

In some embodiments of the methods of the invention it may be particularly desirable to detect expression of a GSEF gene product as well as at least one gene product other GSEF. GSEF expression decreases upon development of metastasis, and may be undetectable in metastatic cells, while GSEF is expressed in non-metastatic and in normal cells. It may also be desirable to detect expression of other gene products in addition to GSEF. For example, E1AF is expressed in non-metastatic, low metastatic potential, high metastatic potential, and metastatic cancer cells but is not expressed at a significant or detectable level in normal cells. Thus detection of an E1AF gene product can serve as a control to distinguish a normal cell from a cancerous cell. In addition, or alternatively, expression of the ESX gene can serve as an additional marker for detection of cells that exhibit the low metastatic phenotype. Expression of ESX is generally detectable in cells of low metastatic potential, but is generally not detectable in cells of high metastatic potential. Detection of GSEF with E1AF and/or ESX thus can provide a more sensitive assay for the classification of the metastatic potential of a cell. The ESX polynucleotide and amino acid sequences are provided in the Sequence Listing as SEQ ID NOS:4 and 5.

Other gene products that can serve as controls or increase the sensitivity of classification of the metastatic phenotype of a cell, as well as gene products that can serve as controls for identification of normal cells (e.g., gene products that are expressed in normal cells but not in cancerous cells, or expressed in normal cells, but not in metastatic cells, etc.) are known in the aft. In addition, the cells can be classified as normal or cancerous based on conventional methodologies such as general morphology as determined by light microscopy. For example, conventional techniques for classifying a cell as cancerous based on morphology can be performed prior to or simultaneously with detection of GSEF expression. Thus, a cell that exhibits abnormal morphology associated with the cancer phenotype, and that expresses a low level of GSEF relative to a normal cells or in which GSEF expression is not detectable is identified as a cell of high metastatic potential.

Methods for qualitative and quantitative detection of polypeptides or nucleic acid in a sample, as well as methods for comparing such to control samples are well known in the art. For example, a variety of different methods for determining the nucleic acid abundance in a sample are known to those of skill in the art, where particular methods of interest include those described in: Pietu et al. *Genome Res.* (1996) 6:492; Zhao et al., *Gene* (1995) 156:207; Soares, *Curr. Opin. Biotechnol.* (1977) 8: 542; Raval, *J. Pharmacol Toxicol Methods* (1994) 32:125; Chalifour et al., *Anal. Biochem* (1994) 216:299; Stolz et al., *Mol. Biotechnol.* (1996) 6:225; Hong et al., *Biosci. Reports* (1982) 2:907; McGraw, *Anal. Biochem.* (1984) 143:29; and WO 97/27317.

The patient from whom the sample is obtained can be apparently healthy, susceptible to disease (e.g., as determined by family history or exposure to certain environmental factors), or can already be identified as having a condition in which altered expression of a gene product of the invention is implicated.

In the assays of the invention, the diagnosis can be determined based on detected GSEF gene product expression levels, and may also include detection of additional diagnostic markers and/or reference sequences. Where the diagnostic method is designed to detect the presence or susceptibility of a patient to metastatic cancer, the assay preferably involves detection of a GSEF gene product and comparing the detected gene product levels to a level associated with a normal sample, to levels associated with a low metastatic. potential sample, and/or to level associated with a high metastatic potential sample. For example, detection of a lower level of GSEF expression relative to a normal level is indicative of the presence in the sample of a cell having high metastatic potential. Given the disclosure provided herein, variations on the diagnostic and prognostic assays described herein will be readily apparent to the ordinarily skilled artisan.

Any of a variety of detectable labels can be used in connection with the various methods of the invention. Suitable detectable levels include fluorochromes, radioactive labels, and the like. Suitable labels include, but are not necessarily limited to, fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. 32P, 35S, 3H; etc. The detectable label can involve a two stage system (e.g., biotin-avidin, hapten-anti-hapten antibody, etc.).

Reagents specific for the polynucleotides and polypeptides of the invention, such as detectably labeled antibodies or detectably labeled nucleotide probes, can be supplied in a kit for detecting the presence of an expression product in a biological sample. The kit can also contain buffers or labeling components, as well as instructions for using the reagents to detect and quantify expression products in the biological sample. Exemplary embodiments of the diagnostic methods of the invention are described below in more detail.

Polypeptide Detection in Diagnosis, Prognosis, Cancer Grading and Cancer Staging In one embodiment, the test sample is assayed for the level of a GSEF polypeptide. Diagnosis can be accomplished using any of a number of methods to determine the absence or presence or altered amounts of the differentially expressed polypeptide in the test sample. For example, detection can utilize staining of cells or histological sections (e.g., from a biopsy sample) with labeled antibodies, performed in accordance with conventional methods. Cells can be permeabilized to stain cytoplasmic molecules. In general, antibodies that specifically bind a differentially expressed polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.). The absence or presence of antibody binding can be determined by various methods, including flow cytometry of dissociated cells, microscopy, radiography, scintillation counting, etc. Any suitable alternative methods can of qualitative or quantitative detection of levels or amounts of differentially expressed polypeptide can be used, for example ELISA, western blot, immunoprecipitation, radioimmunoassay, etc.

In general, the detected level of GSEF polypeptide in the test sample is compared to a level of the differentially expressed gene product in a reference or control sample, e.g., in a normal cell or in a cell having a known disease state (e.g., cell of high metastatic potential).

mRNA Detection

The diagnostic, prognostic, grading, and staging methods of the invention can also or alternatively involve detection of mRNA encoded by a GSEF gene. Any suitable qualitative or quantitative methods known in the art for detecting specific mRNAs can be used. mRNA can be detected by, for example, in situ hybridization in tissue sections, by reverse transcriptase-PCR, or in Northern blots containing poly A+mRNA. One of skill in the art can readily use these methods to determine differences in the size or amount of mRNA transcripts between two samples. For example, the level of mRNA of the invention in a tissue sample suspected of being cancerous, particularly a tissue suspected of being of high metastatic potential, is compared with the expression of the mRNA in a reference sample, e.g., a positive or negative control sample (e.g., normal tissue, cancerous tissue, etc.).

Any suitable method for detecting and comparing mRNA expression levels in a sample can be used in connection with the diagnostic methods of the invention (see, e.g., U.S. Pat. No. 5,804,382). For example, mRNA expression levels in a sample can be determined by generation of a library of expressed sequence tags (ESTs) from the sample, where the EST library is representative of sequences present in the sample (Adams, et al., (1991) *Science* 252:1651). Enumeration of the relative representation of ESTs within the library can be used to approximate the relative representation of the gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein.

Alternatively, gene expression in a test sample can be performed using serial analysis of gene expression (SAGE) methodology (Velculescu et al., *Science* (1995) 270:484). In short, SAGE involves the isolation of short unique sequence tags from a specific location within each transcript. The sequence tags are concatenated, cloned, and sequenced. The frequency of particular transcripts within the starting sample is reflected by the number of times the associated sequence tag is encountered with the sequence population.

Gene expression in a test sample can also be analyzed using differential display (DD) methodology. In DD, fragments defined by specific sequence delimiters (e.g., restriction enzyme sites) are used as unique identifiers of genes, coupled with information about fragment length or fragment location within the expressed gene. The relative representation of an expressed gene with a sample can then be estimated based on the relative representation of the fragment associated with that gene within the pool of all possible fragments. Methods and compositions for carrying out DD are well known in the art, see, e.g., U.S. Pat. Nos. 5,776,683; and 5,807,680.

Alternatively, gene expression in a sample using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry). One exemplary use of arrays in the diagnostic methods of the invention is described below in more detail.

Pattern Matching in Diagnosis Using Arrays

In another embodiment, the diagnostic and/or prognostic methods of the invention involve detection of expression of a selected set of genes in a test sample to produce a test expression pattern (TEP), where the selected set comprises a GSEF gene expression. product. The TEP is compared to a reference expression pattern (REP), which is generated by detection of expression of the selected set of genes in a reference sample (e.g., a positive or negative control sample).

"Reference sequences" or "reference polynucleotides" as used herein in the context of differential gene expression analysis and diagnosis/prognosis refers to a selected set of polynucleotides, which selected set includes at least one or more of the differentially expressed polynucleotides described herein. A plurality of reference sequences, preferably comprising positive and negative control sequences, can be included as reference sequences. Additional suitable reference sequences are found in GenBank, Unigene, and other nucleotide sequence databases (including, e.g., expressed sequence tag (EST), partial, and full-length sequences).

"Reference array" means an array having reference sequences for use in hybridization with a sample, where the reference sequences include all, at least one of, or any subset of the differentially expressed polynucleotides described herein. Usually such an array will include at least 1 different reference sequence. Arrays of interest can further comprise sequences, including polymorphisms, of other genetic sequences, particularly other sequences of interest for screening for a disease or disorder (e.g., cancer, dysplasia, or other related or unrelated diseases, disorders, or conditions). The oligonucleotide sequence on the array will usually be at least about 12 nt in length, and can be of about the length of the provided sequences, or can extend into the flanking regions to generate fragments of 100 nt to 200 nt in length or more.

A "reference expression pattern" or "REP" as used herein refers to the relative levels of expression of a selected set of genes, particularly of differentially expressed genes, that is associated with a selected cell type, e.g., a normal cell, a cancerous cell, a cell exposed to an environmental stimulus, and the like. A "test expression pattern" or "TEP" refers to relative levels of expression of a selected set of genes, particularly of differentially expressed genes, in a test sample (e.g., a cell of unknown or suspected disease state, from which mRNA is isolated).

REPs can be generated in a variety of ways according to methods well known in the art. For example, REPs can be generated by hybridizing a control sample to an array having a selected set of polynucleotides, acquiring the hybridization data from the array, and storing the data in a format that allows for ready comparison of the REP with a TEP. Alternatively, all expressed sequences in a control sample can be isolated and sequenced, e.g., by isolating mRNA from a control sample, converting the mRNA into cDNA, and sequencing the cDNA. The resulting sequence information roughly or precisely reflects the identity and relative number of expressed sequences in the sample. The sequence information can then be stored in a format (e.g., a computer-readable format) that allows for ready comparison of the REP with a TEP. The REP can be normalized prior to or after data storage, and/or can be processed to selectively remove sequences of expressed genes that are of less interest or that might complicate analysis (e.g., some or all of the sequences associated with housekeeping genes can be eliminated from REP data).

TEPs can be generated in a manner similar to REPs, e.g., by hybridizing a test sample to an array having a selected set of polynucleotides, particularly a selected set of differentially expressed polynucleotides, acquiring the hybridization data from the array, and storing the data in a format that allows for ready comparison of the TEP with a REP. The REP and TEP to be used in a comparison can be generated simultaneously, or the TEP can be compared to previously generated and stored REPs.

In one embodiment of the invention, comparison of a TEP with a REP involves hybridizing a test sample with a reference array, where the reference array has one or more reference sequences for use in hybridization with a sample. The reference sequences include all, at least one of, or any subset of the differentially expressed polynucleotides described herein. Hybridization data for the test sample is acquired, the data normalized, and the produced TEP compared with a REP generated using an array having the same or similar selected set of differentially expressed polynucleotides. Probes that correspond to sequences differentially expressed between the two samples will show decreased or increased hybridization efficiency for one of the samples relative to the other.

Reference arrays can be produced according to any suitable methods known in the art. For example, methods of producing large arrays of oligonucleotides are described in U.S. Pat. Nos. 5,134,854, and 5,445,934 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505.

Methods for collection of data from hybridization of samples with a reference arrays are also well known in the art. For example, the polynucleotides of the reference and test samples can be generated using a detectable fluorescent label, and hybridization of the polynucleotides in the samples detected by scanning the microarrays for the presence of the detectable label. Methods and devices for detecting fluorescently marked targets on devices are known in the art. Generally, such detection devices include a microscope and light source for directing light at a substrate. A photon counter detects fluorescence from the substrate, while an x-y translation stage varies the location of the substrate. A confocal detection device that can be used in the subject methods is described in U.S. Pat. No. 5,631,734. A scanning laser microscope is described in Shalon et al., Genome Res. (1996) 6:639. A scan, using the appropriate excitation line, is performed for each fluorophore used. The digital images generated from the scan are then combined for subsequent analysis. For any particular array element, the ratio of the fluorescent signal from one sample (e.g. a test sample) is compared to the fluorescent signal from another sample (e.g., a reference sample), and the relative signal intensity determined.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes.

In general, the test sample is classified as having a gene expression profile corresponding to that associated with a disease or non-disease state by comparing the TEP generated from the test sample to one or more REPs generated from reference samples (e.g., from samples associated with cancer or specific stages of cancer, dysplasia, samples affected by a disease other than cancer, normal samples, etc.). The criteria for a match or a substantial match between a TEP and a REP include expression of the same or substantially the same set of genes, as well as expression of these genes at substantially the same levels (e.g., no significant difference between the samples for a signal associated with a selected reference sequence after normalization of the samples, or at least no greater than about 25% to about 40% difference in signal strength for a given reference sequence). In general for the purposes of the present invention, a pattern match between a TEP and a REP is a match in expression, preferably a match in qualitative or quantitative expression level, of at least a GSEF gene.

Pattern matching can be performed manually, or can be performed using a computer program. Methods for preparation of substrate, matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992.

Cancers Amenable to Diagnosis, Prognosis, Staging and/or Grading Using the Methods of the Invention The method of the invention can be used to detect GSEF expression levels in any cell or tissue sample in which GSEF expression levels may be linked to development of the metastatic phenotype. Of particular interest is the detection of GSEF expression levels in samples taken from breast tissue or from prostate tissue. GSEF expression levels may also be linked to development of the metastatic phenotype in cells or tissue of various origins, including, but not limited to, lung, colon, prostate, liver, trachea, epithelia-derived tissues, etc.

GSEF expression levels can indicate the development of the metastatic phenotype in a variety of cancers that may develop within a single tissue. For example, GSEF expression levels can be used to detect the development of the metastatic phenotype in, and to differentiate between, the various types of breast cancer, prostate cancer, lung cancer, or colon cancer. In one embodiment the methods of the invention involve the diagnosis, prognosis, staging, and/or grading of breast tumors or prostate tumors.

Use of the Methods of the Invention in Breast Cancers

Detection of GSEF expression can be used to differentiate between non-cancerous breast tissue, low metastatic potential, and high metastatic potential breast tissue by analyzing differential gene expression between tissues. Similarly, the expression of GSEF can be used in the diagnosis and management of breast cancer. Determination of the aggressive nature and/or the metastatic potential of a breast cancer can be determined by comparing levels of GSEF expression, which can be compared to levels of another sequence known to vary in cancerous tissue, e.g. ER expression. In addition, detection of GSEF expression levels can be performed in conjunction with detection of levels of steroid hormones (e.g., testosterone or estrogen) or to other hormones (e.g., growth hormone, insulin).

Diagnosis of breast cancer can also involve comparing the expression of a polynucleotide of the invention with the expression of other sequences in non-malignant breast tissue samples in comparison to one or more forms of the diseased tissue. A comparison of expression of one or more polynucleotides of the invention between the samples provides information on relative levels of these polynucleotides as well as the ratio of these polynucleotides to the expression of other sequences in the tissue of interest compared to normal. For example, GSEF expression can be examined in a sample of ductal epithelium and compared to a level of GSEF expression in normal ductal epithelium. A decrease of GSEF expression in the ductal epithelium sample relative to GSEF expression in normal ductal epithelium indicates that the sample contains cells of high metastatic potential.

As well as being used for diagnosis and risk assessment, the expression of the polynucleotides of the invention can be of prognostic value for determining the metastatic potential of a malignant breast cancer, as this molecules are differentially expressed between high and low metastatic potential tissues tumors. The levels of these polynucleotides in patients with malignant breast cancer can compared to normal tissue, malignant tissue with a known high potential metastatic level, and malignant tissue with a known lower level of metastatic potential to provide a prognosis for a particular patient. Such a prognosis is predictive of the extent and nature of the cancer. The determined prognosis is useful in determining the prognosis of a patient with breast cancer, both for initial treatment of the disease and for longer-term monitoring of the same patient. If samples are taken from the same individual over a period of time, differences in polynucleotide expression that are specific to that patient can be identified and closely watched.

The specific types of breast cancer that may be of particular interest are described below.

Ductal Carcinoma In situ (DCIS)

Ductal carcinoma in situ is the most common type of noninvasive breast cancer. In DCIS, the malignant cells have not metastasized through the walls of the ducts into the fatty tissue of the breast. Comedocarcinoma is a type of DCIS that is more likely than other types of DCIS to come back in the same area after lumpectomy, and is more closely linked to eventual development of invasive ductal carcinoma than other forms of DCIS.

Infiltrating (or Invasive) Ductal Carcinoma (IDC)

In IDC, cancerous cells have metastasized through the wall of the duct and invaded the fatty tissue of the breast. At this point, it has the potential to use the lymphatic system and bloodstream for metastasis to more distant parts of the body.

Lobular Carcinoma In situ (LCIS)

While not a true cancer, LCIS (also called lobular neoplasia) is sometimes classified as a type of noninvasive breast cancer. It does not penetrate through the wall of the lobules. Although it does not itself usually become an invasive cancer, women with this condition have a higher risk of developing an invasive breast cancer in the same or opposite breast.

Infiltrating (or Invasive) Lobular Carcinoma (ILC)

ILC is similar to IDC, in that it has the potential to metastasize elsewhere in the body. About 10% to 15% of invasive breast cancers are invasive lobular carcinomas, and can be more difficult to detect by mammogram than IDC.

Inflammatory Breast Cancer

This invasive breast cancer, which accounts for about 1% of all breast cancers, is extremely aggressive. Multiple skin symptoms associated with this cancer are caused by cancer cells blocking lymph vessels or channels in skin over the breast.

Medullary Carcinoma

This special type of infiltrating breast cancer, which presently accounts for about 5% of breast cancers, has a relatively well defined, distinct boundary between tumor tissue and normal tissue. The prognosis for medullary carcinoma is better than for other types of invasive breast cancer.

Mucinous Carcinoma

Mucinous carcinoma originates from mucus-producing cells. The prognosis for mucinous carcinoma is better than for the more common types of invasive breast cancer.

Paget's Disease of the Nipple

This type of breast cancer starts in the ducts and spreads to the skin of the nipple and the areola. It is a rare type of breast cancer, occurring in only 1% of all cases. Paget's disease can be associated with in situ carcinoma, or with infiltrating breast carcinoma. If no lump can be felt in the breast tissue, and the biopsy shows DCIS but no invasive cancer, the prognosis is excellent.

Phyllodes Tumor

This very rare type of breast tumor forms from the stroma of the breast, in contrast to carcinomas which develop in the ducts or lobules. Phyllodes (also spelled phylloides) tumors are usually benign, but are malignant on rare occasions.

Tubular Carcinoma

Accounting for about 2% of all breast cancers, tubular carcinomas are a special type of infiltrating breast carcinoma. They have a better prognosis than usual infiltrating ductal or lobular carcinomas.

Use of the Methods of the Invention in Cancers of Other Origins

In addition to use in diagnosis of breast cancer, detections of GSEF gene product expression levels can be used in the diagnosis, prognosis, grading, and/or stating of cancers of other tissue origins. In general, as noted above, the methods of the invention can be used in conjunction with any tissue in which an alteration in GSEF gene product expression levels is associated with development of a cancer-associated phenotype, e.g., metastasis. Exemplary cancers in which the methods of the invention can find use include, but are not necessarily limited to, prostate cancer, cervical cancers, melanomas, colorectal adenocarcinomas, Wilms' tumor, retinoblastoma, sarcomas, myosarcomas, lung carcinomas, leukemias, such as chronic myelogenous leukemia, promyelocytic leukemia, monocytic leukemia, and myeloid leukemia, and lymphomas, such as histiocytic lymphoma. Of particular interest is the detection of GSEF expression in prostate tissues to facilitate the identification of cancerous prostate cells, as well as the grading and/or staging of such potential prostate tumors.

For example, GSEF gene product expression levels can be used in the diagnosis of prostate cancer, and/or to differentiate between the types or grades of prostate cancer, particularly to distinguish a Stage I or Stage II prostate cancer (non-metastatic or low metastatic potential) from a Stage II (cancer spread outside the prostate capsule) or Stage IV (metastatic) prostate cancer at a early stage (e.g., prior to development of significant metastases). As with breast and other cancers, detection of high metastatic potential cells can also provide information regarding the dangers of recurrence of cancer either before or after therapy (e.g., chemotherapy, surgery, etc.).

GSEF gene product expression levels can also be used in the diagnosis of lung cancers, and/or to differentiate between the types of lung cancers. The two main types of lung cancer are small cell carcinomas and nonsmall cell carcinomas. Small cell carcinoma (also called oat cell carcinoma) usually starts in one of the larger bronchial tubes, grows fairly rapidly, and is likely to be large by the time of conventional diagnosis. Nonsmall cell lung cancer (NSCLC) is made up of three general subtypes: epidermoid carcinoma, adenocarcinoma, and large cell carcinoma. Epidermoid carcinoma (also called squamous cell carcinoma) usually starts in one of the larger bronchial tubes and grows relatively slowly. Adenocarcinoma starts growing near the outside surface of the lung and can vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindromal, mucoepidermoid, and malignant mesothelioma.

GSEF gene product expression levels can also be used to detect, diagnose, and/or differentiate colon cancers. The major types of colon cancer include familial adenomatous polyposis (FAP), Gardner's syndrome, and hereditary nonpolyposis colon cancer (HNPCC. FAP is associated with hundreds or even thousands of polyps in the patient's colon and rectum, which polyps usually first appear during the teenage years. Cancer nearly always develops in one or more of these polyps between the ages of 30 and 50. Like FAP, Gardner's syndrome is associated with polyps and colorectal cancers that develop at a young age, and is also associated with benign tumors of the skin, soft connective tissue, and bones. HNPCC patients tend to develop colorectal cancer at a young age, without first having many polyps. In addition, recent research has found an inherited tendency to developing colorectal cancer among some Jews of Eastern European descent, which population would benefit from prognostic and diagnosis methods for early detection of the development of the metastatic phenotype.

Detection of Polymorphisms and Rational Therapy

In one embodiment, the nucleic acid and/or polypeptide compositions described herein are used to detect the presence of polymorphisms in the sequence, or variation in the expression of the subject genes, e.g., genotyping. Such analysis may be performed to determine whether a particular polymorphism is associated with a disease state or genetic predisposition to a disease state, particularly conditions, disorders, or diseases associated with GSEF (e.g., metastatic cancers) Analysis of sequence encoding a gene product of interest, e.g., GSEF, or analysis of a sequence of a promoter or other regulatory sequence that provide for expression of such a gene product may also be performed for pharmacogenetic analysis to assess the association between an individual's genotype and that individual's ability to react to a therapeutic agent. Differences in target sensitivity can lead to toxicity or therapeutic failure. Relationships between polymorphisms in expression levels or specificity can be used to optimize therapeutic dose administration.

Genetic polymorphisms can be identified in a GSEF gene (e.g., within a coding region of a GSEF genomic sequence, and/or within a regulatory domain of such a sequence), and the nucleic acids comprising the polymorphic sequences used to screen patients for altered reactivity and adverse side effects in response to drugs that act on GSEF polypeptides. GSEF genotyping can be performed by DNA or RNA sequence and/or hybridization analysis of any convenient sample from a patient, e.g. biopsy material, blood sample, scrapings from cheek, etc. A nucleic acid sample from an individual is analyzed for the presence of polymorphisms in GSEF, particularly those that affect the activity, responsiveness to a therapeutic agent (e.g., inhibitor or enhancer of activity), or expression of GSEF. Specific sequences of interest include any polymorphism that lead to changes in basal expression in one or more tissues, to changes in the modulation of GSEF expression, or alterations in GSEF specificity and/or activity. Of particular interest are those changes that lead to a decrease in GSEF expression or activity, which decrease is associated with development of the metastatic phenotype.

The effect of a polymorphism in a GSEF gene sequence on the response to a particular agent may be determined by in vitro or in vivo assays. Such assays may include monitoring during clinical trials, testing on genetically defined cell lines, etc. The response of an individual to the agent can then be predicted by determining the GSEF genotype with respect to the polymorphism. Where there is a differential distribution of a polymorphism by racial background, guidelines for drug administration can be generally tailored to a particular ethnic group. Such studies can provide an understanding of the individual's nonresponsiveness to a therapy that has proven effective in a large number of patients having a similar syndrome (e.g., to facilitate identification of patients that are or are likely to be nonresponsive to administration of an inhibitor of a gene product that interferes with GSEF activity).

Biochemical studies may be performed to determine whether a sequence polymorphism in a GSEF coding region or control regions is associated with disease, for example the association of a GSEF polymorphisms with specific diseases or conditions, e.g., metastatic cancers, including but not limited to breast cancer, prostate cancer, etc. Disease associated polymorphisms may include deletion or truncation of the gene, mutations that alter expression level, that affect GSEF activity, etc.

A number of methods are available for analyzing nucleic acids for the presence of a specific sequence. Where large amounts of DNA are available, genomic DNA is used directly. Alternatively, the region of interest is cloned into a suitable vector and grown in sufficient quantity for analysis. The nucleic acid may be amplified by conventional techniques, such as the polymerase chain reaction (PCR), to provide sufficient amounts for analysis. The use of the polymerase chain reaction is described in Saiki et al. (1985) *Science* 239:487, and a review of current techniques may be found in Sambrook et al. Molecular Cloning: A Laboratory Manual, CSH Press 1989, pp.14.2–14.33. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al. (1990) *Nucl. Acids Res.* 18:2887–2890; and Delahunty et al. (1996) *Am. J. Hum. Genet.* 58:1239–1246. A detectable label may be included in an amplification reaction. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

In one embodiment of the invention, an array of oligonucleotides are provided, where discrete positions on the array are complementary to one or more of the provided polymorphic sequences, e.g. oligonucleotides of at least 12 nt, frequently 20 nt, or larger, and including the sequence flanking the polymorphic position. Such an array may comprise a series of oligonucleotides, each of which can specifically hybridize to a different polymorphism. For examples of arrays, see Hacia et al. (1996) *Nature Genet.* 14:441–447; Lockhart et al. (1996) *Nature Biotechnol.* 14:1675–1680; and De Risi et al. (1996) *Nature Genet.* 14:457–460.

Screening for polymorphisms in a GSEF amino acid sequence may be based on the functional or antigenic characteristics of the protein. Protein truncation assays are useful in detecting deletions that may affect the biological activity of the protein. Various immunoassays designed to detect polymorphisms in a GSEF proteins may be used in screening. Where many diverse genetic mutations lead to a particular disease phenotype, functional protein assays have proven to be effective screening tools.

Antibodies specific for a GSEF gene product may be used in staining or in immunoassays. Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

PHARMACEUTICAL COMPOSITIONS AND THERAPEUTIC USES

Pharmaceutical compositions can comprise GSEF polypeptides, antibodies, or GSEF polynucleotides. The pharmaceutical compositions comprise a therapeutically effective amount of either polypeptides, antibodies, or polynucleotides of the claimed invention. In general, the pharmaceutical compositions are based upon molecules that can enhance GSEF biological activity (e.g., by increasing the amount of GSEF present in a cell (e.g., by increasing expression of a GSEF gene product in a cancerous cell, e.g., by introducing a GSEF-encoding sequence into the cell for expression therein)), or by inhibiting a GSEF inhibitor) in order to inhibit, delay, or otherwise interfere with the development of metastasis in a cancerous cell. Similarly, methods for treatment, e.g., inhibition of development of the metastatic phenotype or reversal of the metastatic phenotype, employ such pharmaceutical compositions that enhance GSEF biological activity.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation is determined by routine experimentation and is within the judgment of the clinician. For purposes of the present invention, an effective dose will generally be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles. Typically, the therapeutic compositions are prepared as injectables, either as, liquid solutions or suspensions; solid forms suitable for solution in, or suspension in, liquid vehicles prior to injection can also be prepared. Liposomes are included within the definition of a pharmaceutically acceptable carrier.

Delivery Methods

Once formulated, the compositions of the invention can be (1) administered directly to the subject (e.g., as polynucleotide or polypeptides) or (2) delivered ex vivo, to cells derived from the subject (e.g., as in ex vivo gene therapy, see, e.g., WO 93/14778). In general, the therapy will involve direct delivery of the pharmaceutical composition to the subject. Direct delivery of the compositions will generally be accomplished by injection, either subcutaneously, intraperitoneally, intravenously or intramuscularly, or delivered to the interstitial space of a tissue. The compositions can also be administered directly into a tumor or lesion. Other modes of administration include oral and pulmonary administration, suppositories, and transdermal applications, needles, and gene guns or hyposprays. Dosage treatment can be a single dose schedule or a multiple dose schedule.

Various methods can be used to administer the therapeutic composition directly to a specific site in the body. For example, a small metastatic lesion is located and the therapeutic composition injected several times in several different locations within the body of the tumor. Alternatively, arteries which serve a tumor are identified, and the therapeutic composition injected into such an artery, in order to deliver the composition directly into the tumor. A tumor that has a necrotic center is aspirated and the composition injected directly into the now empty center of the tumor. X-ray imaging can be used to assist in certain of the above delivery methods.

The therapeutic compositions can also be delivered using receptor-mediated targeted delivery. For examples of such receptor-mediated delivery, see, e.g., Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. (USA) (1990) 87:3655; Wu et al., J. Biol. Chem. (1991) 266:338.

Where the therapeutic composition comprises a polynucleotide, the polynucleotides can be administered in a range of about 100 ng to about 200 mg of DNA for local administration. Concentration ranges of about 500 ng to about 50 mg, about 1 $\mu$g to about 2 mg, about 5 $\mu$g to about 500 $\mu$g, and about 20 $\mu$g to about 100 $\mu$g of DNA can also be used. The actual dosage will vary according to a variety of factors that will be readily appreciated by the ordinarily skilled artisan, such as efficiency of transformation and expression. Where greater expression is desired over a larger area of tissue, larger amounts of polynucleotides or the same amounts readministered in a successive protocol of administrations, or several administrations to different adjacent or close tissue portions of, for example, a tumor site, can be performed. In all cases, routine experimentation in clinical trials will determine specific ranges for optimal therapeutic effect.

Various vectors and protocols to accomplish delivery of polynucleotides to, and expression in, a cell in vivo are known in the art. The polynucleotide delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Gene therapy vehicles for delivery of constructs including a coding sequence of a GSEF polypeptide can be administered either locally or systemically. Expression of such GSEF coding sequences can be induced using endogenous mammalian or heterologous promoters (i.e., promoters that are derived from a source other than that of the GSEF gene to be expressed), and can be either constitutive or regulated.

Where a viral vector is used, the recombinant viral vector can be based upon, for example, a retroviral vector, alphavirus-based vectors (e.g., vectors based on Sindbis virus, Semliki forest virus, Ross River virus, Venezuelan equine encephalitis virus, etc.), parvoviral-vector (e.g., adeno-associated virus (AAV)), or an adenoviral vector. Retroviral vectors may be less desirable where the target cell is rapidly dividing, e.g., where the target cell is a rapidly dividing cancerous cell.

Non-viral vehicles and methods can be employed. Such vehicles and methods can be based upon, for example, liposomes, lipid:DNA complexes, polycationic condensed DNA (linked or unlinked to killed adenovirus), ligand linked DNA, photopolymerized hydrogel materials; naked DNA; hand-held gene transfer particle guns, ionizing radiation (see, e.g., U.S. Pat. No. 5,206,152), nucleic charge neutralization or fusion with cell membranes. Additional approaches are described in Philip, Mol. Cell Biol. (1994) 14:2411, and in Woffendin, Proc. Natl. Acad. Sci. (1994) 91:1581.

MODULATION OF GENE EXPRESSION

The GSEF genes, gene fragments, or the encoded protein or protein fragments are useful in gene therapy to treat disorders associated with defects in a GSEF gene. GSEF genes, gene fragments, promoter elements, or the encoded protein or protein fragments are of particular interest. Expression vectors may be used to introduce the desired GSEF polypeptide-encoding gene into a cell. Such vectors generally have convenient restriction sites located near the promoter sequence to provide for the insertion of nucleic acid sequences. Transcription cassettes may be prepared comprising a transcription initiation region the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The GSEF polypeptide-encoding gene or may be introduced into tissues or host cells by any number of routes, including, but not necessarily limited to, viral infection, direct injection, microinjection, or fusion of vesicles. Direct injection of DNA for expression is described in, for example, U.S. Pat. No. 5,580,859. Jet injection may also be used for intramuscular administration, as described by Furth et al. (1992) Anal. Biochem. 205:365–368. The DNA may be coated onto gold microparticles, and delivered intradermally by a particle bombardments device, or "gene gun" as described in the literature (see, for example, Tang et al. (1992) Nature 356:152–154), where gold microprojectiles are coated with the GSEF DNA, then bombarded into skin cells. Use of liposomes for delivery of DNA into a living cell is also known in the art, see, e.g., U.S. Pat. No. 4,394,448.

Antisense molecules can be used to down-regulate expression of a GSEF in cells, e.g., to study the mechanisms of GSEF in development of the metastatic phenotype, e.g., to identify gene products expressed in the absence of GSEF expression. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be introduced, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) Nature Biotechnol. 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate; 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidin. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. maybe used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995) Nucl. Acids Res. 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) Appl. Biochem. Biotechnol. 54:43–56.

GENETICALLY ALTERED CELL OR ANIMAL MODELS FOR GSEF FUNCTION

The subject nucleic acids can be used to generate transgenic animals or site specific gene modifications in cell lines. Transgenic animals may be made through homologous recombination, where the normal GSEF locus is altered. Alternatively, a nucleic acid construct (e.g., encoding a human GSEF cDNA or promoter) is randomly integrated into the genome. Vectors for stable integration include plasmids, retroviruses and other animal viruses, YACs, and the like. Transgenic animals may be homozygous or heterozygous for the gene modification, and may be a "knock-out" transgenic animal (i.e., a transgenic animal in which one allele of the corresponding GSEF-encoding gene is rendered nonfunctional) and/or a "knock-in" transgenic animal (i.e., a transgenic animal having at least one copy of a recombinant GSEF-encoding sequence present in its genome, e.g., in its germ line DNA). Methods for generating transgenic animals are well known in the art.

The modified cells or animals are useful in the study of the function and regulation. of GSEF, particularly with respect to study of the development of the metastatic phenotype, as well as models to develop and test cancer therapies. For example, a series of small deletions and/or substitutions may be made in the GSEF gene to determine the role of GSEF, binding to agents or candidate agents for modulation of GSEF function, etc. Of interest are the use of the nucleic acid compositions of the invention to construct transgenic animal models for conditions or disorders associated with defects in GSEF where expression of GSEF is specifically reduced or absent. Specific constructs of interest include anti-sense GSEF that will inhibit expression of GSEF; expression of dominant negative GSEF mutations; etc. One may also provide for expression of the GSEF gene or variants thereof in cells or tissues where it is not normally expressed or at abnormal times of development.

DNA constructs for homologous recombination can comprise at least a portion of the selected GSEF-encoding gene with the desired genetic modification, and can further comprise regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) *Methods Enzymol.* 185:527–537.

Transgenic animals can be generated using any suitable method available in the art. For example, transgenic animals can be generated by using embryonic stem (ES) cells. To this end an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having a heterozygous modification are mated to produce homozygous progeny. If the gene alterations cause lethality at some point in development, tissues or organs can be maintained as allogeneic or congenic grafts or transplants, or in in vitro culture. The transgenic animals may be any, non-human mammal, such as laboratory animals, domestic animals, etc. The transgenic animals may be used in functional studies, drug screening, etc., e.g. to determine the effect of a candidate drug on GSEF or related gene activation, oncogenesis, etc.

SCREENING FOR AGENTS THAT ALTER ACTIVITY OF GSEF AND/OR GENE PRODUCTS REGULATED BY GSEF

GSEF expression is associated with suppression of development of the metastatic phenotype. Thus, agents of interest in the present invention for therapy or for study of the role of GSEF and development of cancer therapies are designed to modulate (e.g., inhibit or enhance, preferably enhance in the case of therapy) GSEF activity in suppression of metastasis. Agents that enhance biological activity of GSEF are of particular interest for use in therapy to inhibit metastasis or development of metastasis. In addition, since GSEF acts as a regulator of the expression, gene products that are affected in relative expression levels by GSEF activity are also of interest as therapeutic targets. Thus, candidate agents that modulate the activity of gene products that exhibit enhanced or decreased expression in response to GSEF activity are also of interest in the present invention.

The subject polypeptides may be used in in vitro and in vivo models to test the specificity of novel candidate compounds, and of analogs and derivatives of compounds known to act on GSEF. The subject polypeptides may be used in such assays in their native form (e.g., full-length), or may be modified by sequence deletion, insertion, substitution, etc. Use of modified GSEF in such screening assays can facilitate identification of, for example, regions of the polypeptide that are important in normal biological function of the polypeptide, identification of especially suitable target sites, for drug interaction, and/or identification of gene products that have their expression regulated. (e.g., upregulated or downregulated) by GSEF activity that may be suitable drug targets. Thus such models facilitate rationale drug design for the development of compounds that specifically inhibit or enhance biological activity of the various GSEF.

In one embodiment, drug screening is performed using an in vitro model, a genetically altered cell or animal, or purified GSEF protein, either as monomers, homomultimers or heteromultimers. One can identify ligands or substrates that bind to, modulate or mimic the action of GSEF, and/or that act on other genes or gene product that facilitate or inhibit GSEF activity, or that exhibit activities that are modulated by GSEF activity. For example, drug screening can identify agents that provide a replacement for GSEF function in abnormal cells having relatively low GSEF activity levels (e.g. cells having high metastatic potential). Of particular interest are screening assays for agents that have a low toxicity for human cells. A wide variety of assays may be used for this purpose, including monitoring GSEF activity levels in the presence of candidate agent, labeled in vitro agent-protein binding assays, electrophoretic mobility shift assays, immunoassays for protein binding, and the like. The purified protein may also be used for determination of three-dimensional crystal structure, which can be used for modeling intermolecular interactions.

In one embodiment of particular interest, the screening method involves the use of a high potential metastatic cell line (e.g., MDA-MB-435) stably transfected with GSEF. Expression of GSEF in the high potential metastatic cell line facilitates reversion of the cell to a low metastatic potential cell. The relative expression levels of genes in the GSEF-reverted cell line can be compared to the expression levels of genes in the parent cell line (i.e., the high metastatic potential cell), as well as to low metastatic potential cells and normal cells, to identify those gene products that are differentially expressed in the presence and absence of GSEF expression or activity. Such differentially expressed genes represent potential therapeutic targets that act downstream of GSEF. In short, GSEF can be used to turn on and to turn off expression of genes that can have a role in development or inhibition of the metastatic phenotype.

The term "agent" as used herein describes any molecule, e.g. protein or pharmaceutical, with the capability of altering or mimicking the physiological function of GSEF or of a gene regulated by GSEF. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Of particular interest in the present invention is the identification of agents that substantially specifically affect GSEF biological activity. Agents that enhance GSEF activity, e.g., by increasing GSEF expression, by mimicking GSEF activity, and/or by inhibiting an endogenous inhibitor of GSEF activity, thus are useful in the treatment of cancer, particularly metastatic or high potential metastatic cancer, particularly breast cancer.

The compounds having the desired pharmacological activity may be administered in a physiologically acceptable carrier to a host in a variety of ways, orally, topically, parenterally e.g. subcutaneously, intraperitoneally, by viral infection, intravascularly, etc. Depending upon the manner of introduction, the compounds may be formulated in a variety of ways. The concentration of therapeutically active compound in the formulation may vary from about 0.1–100 wt. %. The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

Characterization of Human Breast Carcinoma (HBC) Cell Lines Before and After the Mesenchymal Transition The expression of the mesenchymal filament vimentin (VIM), is a prognostic marker for ductal breast carcinoma and has been associated significantly with poor 5-year survival (Domagala (1996) Clin. Cancer Res. 2:147–154). Positive VIM staining is only observed in the myoepithelium of normal breast, with clustered staining detected in the primary tumor. More advance infiltrating carcinomas exhibit the strongest vimentin staining, indicating a transition of gene expression to a more mesenchymal pattern.

To establish an in vitro model system for metastasis we used a panel of human breast carcinoma (HBC) cell lines, which have been previously characterized for their tumor formation as well as metastasis formation potential in nude mice. The characteristics of these cell lines are briefly described in the table below.

| Cell Line | Characteristics |
| --- | --- |
| MDA-MB-435 | High metastatic potential (macrometastases) Metastatic ductal carcinoma; isolated from pleural effusion |
| MDA-MB-231 | High metastatic potential (micrometastases) Adenocarcinoma; isolated from pleural effusions (ATCC HTB 26) |
| ALAB | High metastatic potential (micrometastases) Metastatic ductal carcinoma |
| MDA-MB-468 | Low metastatic potential Adenocarcinoma; isolated from metastasis to brain |
| MDA-MD-361 | Low metastatic potential; Estrogen receptor positive Adenocarcinoma; isolated from metastasis to brain (ATCC HTB 27). |
| ZR-75-1 | Low metastatic potential; Estrogen receptor positive |
| MCF-7 | Low metastatic potential; Estrogen receptor positive Derived from a pleural effusion of a breast adenocarcinoma (ATCC HTB 22) |
| MDA-MD-453 | Non-metastatic (does not form primary tumors) |
| SK-BR-3 | Non-metastatic (does not form primary tumors) Adenocarcinoma; isolated from pleural effusion (ATCC HTB 30) |

| Cell Line | Characteristics |
|---|---|
| HS578Bst | Primary cell line isolated from human breast; fibroblast-like cell (ATCC HTB-124; 6228) |

Cells were categorized as "high metastatic potential" or "low metastatic potential according to the development of primary tumors and metastases in a scid mouse model. In short, five week old scid CB-17 mice were anesthetized and a small incision made to expose the mammary fat pad. Approximately $2.5 \times 10^6$ cells were injection. Mice injected with MCF-7 cells received a subcutaneous pellet releasing 12-β-estradiol (0.36 mg over a period of 60 days). Other estrogen receptor (ER)-positive cell lines such as ZR-75-1 and MDA-MB-361 did not require exogenous estradiol for tumor growth. Tumor growth was monitored by weekly examination and caliper measurement. To examine the potential of specific human breast cancer cell lines to form distant metastases, primary tumors were surgically removed after 32 to 40 days (for ER-negative cell lines MDA-MB-231, MDA-MB-435, and ALAB; tumor volume 600 to 1,000 mm$^3$) or 60 days (for ER-positive cell lines MCF-7, ZR-75-1, and MDA-MB-361; tumor volumes 60 to 100 mm$^3$). 42 days after removal of primary tumors, mice were sacrificed and inspected for the presence of lung metastasis by haematoxylin and eosin staining after embedding into OCT gel (Sakura Finetek).

Cells identified as high metastatic potential were those cells that produced metastases in lung (MDA-MB-435, MDA-MB-231, and ALAB). MDA-MB-435 rapidly form primary tumors and macrometastases in the lung after resection of the primary tumor whereas MDA-MB-231 and ALAB form micrometastases. Cells that formed primary tumors but did not form detectable metastases in the lung were classified as low metastatic potential (MDA-MB-468, MDA-MB-361, ZR-75-1, MCF-7, and MDA-MB-453). Cells that did not form primary tumors, such as SK-BR-3 were classified as non-metagtatic.

In order to analyze the expression phenotype of these cell lines in the context of epithelial to mesenchymal transition (EMT), immunoblot analysis was performed in order to determine the expression status of a series of breast cancer markers including the mesenchymal filament vimentin (FIG. 1). Interestingly two of the three high metastatic cell lines revealed strong vimentin expression whereas all low metastatic cell lines were vimentin negative, indicating that these cell lines shifted to a more mesenchymal phenotype. Cytokeratin 8, 18, and 19 were used as markers for simple epithelium and showed a decreased expression in the more aggressive high metastatic cell lines. All nine cell lines were negative for the myoepithelial marker Cytokeratin 17 (data not shown). Surprisingly Her-2/neu expression was inversely correlated with the ability to form tumors after injection in the mammary pad of nude mice, and showed strongest expression in the non tumor forming cell line SK-BR-3.

Taken together, the data demonstrate that the mesenchymal transition is at least partially conserved in these HBC cell lines and correlates with a more invasive phenotype. Furthermore, this panel of HBC cell lines can serve as a model system to identify gene expression changes associated with the EMT and the metastatic potential.

Example 2

Identification and Cloning of GSEF, an ETS Transcription Factor

To advance our understanding of the molecular regulation of invasiveness in EMT-associated breast carcinoma progression, an extensive gene expression profiling study was performed using the above-characterized HBC cell lines. Since ETS transcription factors have been implicated mechanistically in the progression of breast carcinoma, and have been associated with cell differentiation, carcinogenesis and cell proliferation, the study focused on the ETS transcription factor family. During the course of this study, an EST (GenBank Accession No. AA662164). A PCR approach was used to obtain the full-length cDNA using a breast cDNA library. Since later studies showed a specific expression profile in tissue derived from simple epithelium of human exocrine glands, the gene identified was termed gland-specific Ets transcription factor (GSEF).

The sequence of the full length cDNA as well as the 5' promoter region obtained by 5' RACE are shown in FIGS. 2A–2B. The predicted transcriptional start site, determined by sequence analysis of 5' RACE clones lies 434 bases upstream of the initiation codon. Consistent with the 5' RACE analysis, a TATA box was identified 24 bases 5' of the predicted RNA start site. In addition a consensus initiator sequence overlapping the start site was found, suggesting again that the obtained sequence contains the core promoter. A series of putative ETS binding sites were identified in this promoter fragment (FIG. 2A bold letters). Sequence analysis of the GSEF cDNA revealed an open reading frame of 335 amino acids with an ETS domain localized at the C-terminus (FIG. 2B).

Example 3

Differential Expression of GSEF in High Metastatic Potential and Low Metastatic Potential Cells as Determined by cDNA Library Comparisons The relative expression levels of the GSEF gene was assessed in several cDNA libraries prepared from low metastatic potential breast cells and from high metastatic potential breast cell lines. The table below provides a description of these libraries, including the shortened library name (used hereafter), the MRNA source used to prepared the cDNA library, the "nickname" of the library that is used in the tables below (in quotes), and the approximate number of clones in the library.

Description of cDNA Libraries

| Library | Description | Number of Clones in this Clustering |
|---|---|---|
| 3 | MDA-MB-231 Human Breast Cancer Cell Line, High Metastatic Potential; micro-metastasis in lung "High Met Breast" | 319306 |
| 4 | MCF7 Human Breast Cancer Cell, Non Metastatic "Low Met Breast" | 328941 |

The MDA-MB-231 cell line was originally isolated from pleural effusions (Cailleau, *J. Natl. Cancer. Inst.* (1974) 53:661), is of high metastatic potential, and forms poorly differentiated adenocarcinoma grade II in nude mice consistent with breast carcinoma. The MCF7 cell line was derived from a pleural effusion of a breast adenocarcinoma and is non-metastic (e.g., is of low metastatic potential). These cell lines are well-recognized in the art as models for the study of human breast cancer (see, e.g., Chandrasekaran et al. *Cancer Res.* (1979) 39:870; Gastpar et al., *J Med Chem* (1998) 41:4965; Ransom et al., *Br J Cancer* (1998) 77:1586; Kuang et al., *Nucleic Acids Res* (1998) 26:1116.

Each of the libraries is composed of a collection of cDNA clones that in turn are representative of the mRNAs expressed in the indicated mRNA source. Methods for generating cDNA libraries from isolated mRNA are well known in the art. In order to facilitate the analysis of the millions of sequences in each library, the sequences were assigned to clusters. The concept of "cluster of clones" is derived from a sorting/grouping of cDNA clones based on their hybridization pattern to a panel of roughly 300 7 bp oligonucleotide probes (see Drmanac et al., *Genomics* (1996) 37(1):29). Random cDNA clones from a tissue library are hybridized at moderate stringency to 300 7 bp oligonucleotides. Each oligonucleotide has some measure of specific hybridization to that specific clone. The combination of 300 of these measures of hybridization for 300 probes equals the "hybridization signature" for a specific clone. Clones with similar sequence will have similar hybridization signatures. By developing a sorting/grouping algorithm to analyze these signatures, groups of clones in a library can be identified and brought together computationally. These groups of clones are termed "clusters". Depending on the stringency of the selection in the algorithm (similar to the stringency of hybridization in a classic library cDNA screening protocol), the "purity" of each cluster can be controlled. For example, artifacts of clustering may occur in computational clustering just as artifacts can occur in "wet-lab" screening of a cDNA library with 400 bp cDNA fragments, at even the highest stringency. The stringency used in the implementation of cluster herein provides groups of clones that are in general from the same cDNA or closely related cDNAs. Closely related clones can be a result of different length clones of the same cDNA, closely related clones from highly related gene families, or splice variants of the same cDNA.

Differential expression for a selected cluster was assessed by first determining the number of cDNA clones corresponding to the selected cluster in the first library (e.g., "high met breast"), and the determining the number of cDNA clones corresponding to the selected cluster in the second library (e.g., "low met breast"). Differential expression of the selected cluster in the first library relative to the second library is expressed as a "ratio" of percent expression between the two libraries. In general, the "ratio" is calculated by: 1) calculating the percent expression of the selected cluster in the first library by dividing the number of clones corresponding to a selected cluster in the first library by the total number of clones analyzed from the first library; 2) calculating the percent-expression of the selected cluster in the second library by dividing the number of clones corresponding to a selected cluster in a second library by the total number of clones analyzed from the second library; 3) dividing the calculated percent expression from the first library by the calculated percent expression from the second library. If the "number of clones" corresponding to a selected cluster in a library is zero, the value is set at 1 to aid in calculation. The formula used in calculating the ratio takes into account the "depth" of each of the libraries being compared, i.e., the total number of clones analyzed in each library.

In general, a polynucleotide is said to be significantly differentially expressed between two samples when the ratio value is greater than at least about 2, preferably greater than at least about 3, more preferably greater than at least about 5, where the ratio value is calculated using the method described above. The significance of differential expression is determined using a z score test (Zar, *Biostatistical Analysis*, Prentice Hall, Inc., USA, "Differences between Proportions," pp 296–298 (1974).

The GSEF gene was analyzed in this manner to determine if GSEF is differentially expressed between cells derived from high metastatic potential breast cancer tissue and low metastatic breast cancer cells. The GSEF specifc cluster was 185412 and Forty-one clones corresponding to the GSEF gene were identified in the MCF7 library ("low met breast"), while the MDA-MB-231 library ("high met breast) contained no clones corresponding to GSEF. These findings indicate that GSEF is differentially expressed between high metastatic potential breast cells and low metastatic potential breast cells. As illustrated in the table below, the ratio of expression is about 40.

| Cell Line | Clones Corresponding to GSEF Cluster No.: 185412 | Ratio of "Low Met Breast" Expression to "High Met Breast" Expression |
|---|---|---|
| MDA-MB-231 "High Met Breast" (Clones in lib319306) | 0 | 40.19 |
| MCF7 "Low Met Breast" (Clones in lib: 328941) | 41 | |

These data indicate the GSEF is expressed at a higher level in breast cells of low metastatic potential than in breast cells of high metastatic potential.

Example 4

GSEF is Normally Expressed as a Prostate-Specific and Breast-Specific Factor

GSEF expression was analyzed using both an RNA Master Blot (Clontech) and an RNA tissue blot (In Vitrogen). The RNA tissue blot was prepared from various tissues according to methods well known in the art. In short, Northern blot analysis was performed using 20–30 µg total RNA isolated by guanidinium thiocyanate/phenol chloroform extraction from cell lines, from primary tumors, or from metastases in liver. Primary tumors and liver metastases were developed from cell lines injected into scid mice according to methods well known in the art. Plasmids containing either the full-length cDNA clone of GSEF (1-1894 bp cloned into pCR2.0-TA. Vector (In Vitrogen)) or the full-length cDNA of E1AF (2 kb coding region) were radiolabeled and hybridized at 65° C. in Express-hyb (Clontech).

Figure 4:
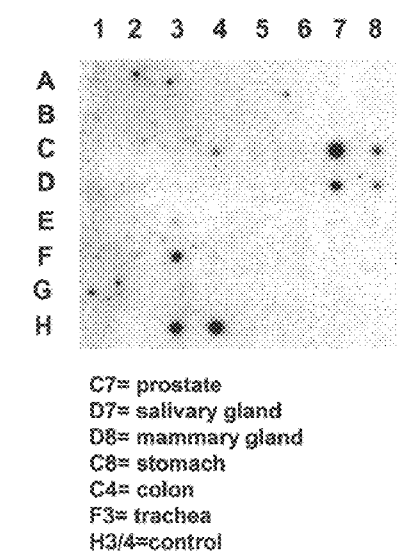
FIG. 4 is a photograph of an RNA tissue blot showing GSEF expression in human heart, brain, placenta, lung, liver, skeletal muscle, kidney, pancreas, spleen, thymus, prostate, testes, ovary, small intestine, colon, and peripheral blood.

The results are shown in FIGS. 3 and 4. In FIG. 4, C7 is prostate; D7 is salivary gland; D8 is mammary gland; C8 is stomach; C4 is colon; F3 is trachea; and H3 and H4 are positive controls. GSEF expression is detected as a band of approximately 2.4 kb.

According to the RNA Master blot and RNA tissue blot, GSEF is expressed primarily in prostate tissue. A relatively low level of GSEF expression was detected in stomach, salivary gland, mammary gland, and trachea. One common feature of these tissues is that they are all associated with secretory functions, suggesting that GSEF is specific for secretory epithelium. To test this hypothesis, in situ hybridization experiments were performed using normal breast tissue and tumor tissue. GSEF expression was detected in luminal or simple epithelial cells of normal breast glands.

These cells are also characterized by expression of cytokeratin 8, 18 and 19 (for review see R. Moll, (1998) Subcell. Biochem. 31:205–262). GSEF expression as detected by immunoblot analysis was perfectly correlated with GSEF expression of these simple epithelia-specific cytokeratins.

Taken together these data indicate that GSEF is a ETS homolog specific for simple epithelium of hormone responsive secretory glands (e.g., prostate and mammary glands), a cell type most commonly associated with common adenocarcinomas Example 5

Differential Expression of GSEF in Breast Cancer Cell Lines Detected by Northern Blot To further investigate the differential expression of GSEF, ESX, and E1AF, in breast cancer, expression of these genes was investigated using both Northern and Western blots prepared from a panel of human breast cancer cell lines with defined metastatic phenotypes.

In order to assess expression at the RNA level, expression of these genes was detected in RNA isolated from each of the cell lines, and from cells of primary tumors or metastases according to methods well known in the art, and expression of GSEF, ESX, E1AF, and β-actin (control) detected. As discussed above, E1AF is implicated as an activator of the metastatic phenotype. Expression of the ESX gene was also detected in parallel samples using a probe based on the sequence in GenBank Accession No. U66894. ESX is a Ets domain-containing gene that is overexpressed early during human breast tumorigenesis (Chang et al. (1997) *Oncogene* 14:1617–1622). Plasmids containing either the full-length cDNA clone of GSEF (1-1894 bp cloned into pCR2.0-TA Vector (In Vitrogen)) or the full-length cDNA of E1AF (2 kb coding region) were radiolabeled and hybridized at 65° C. in Express-hyb (Clontech). expression of the ESX gene was also detected in parallel samples using a probe based on the sequence in GenBank Accession No. U66894. ESX is a Ets domain-containing gene that is overexpressed early during human breast tumorigenesis (Chang et al. (1997) *Oncogene* 14:1617–1622). Plasmids containing full length cDNA of β-actin and ESX were labeled as described for the GSEF probe.

Figure 5:
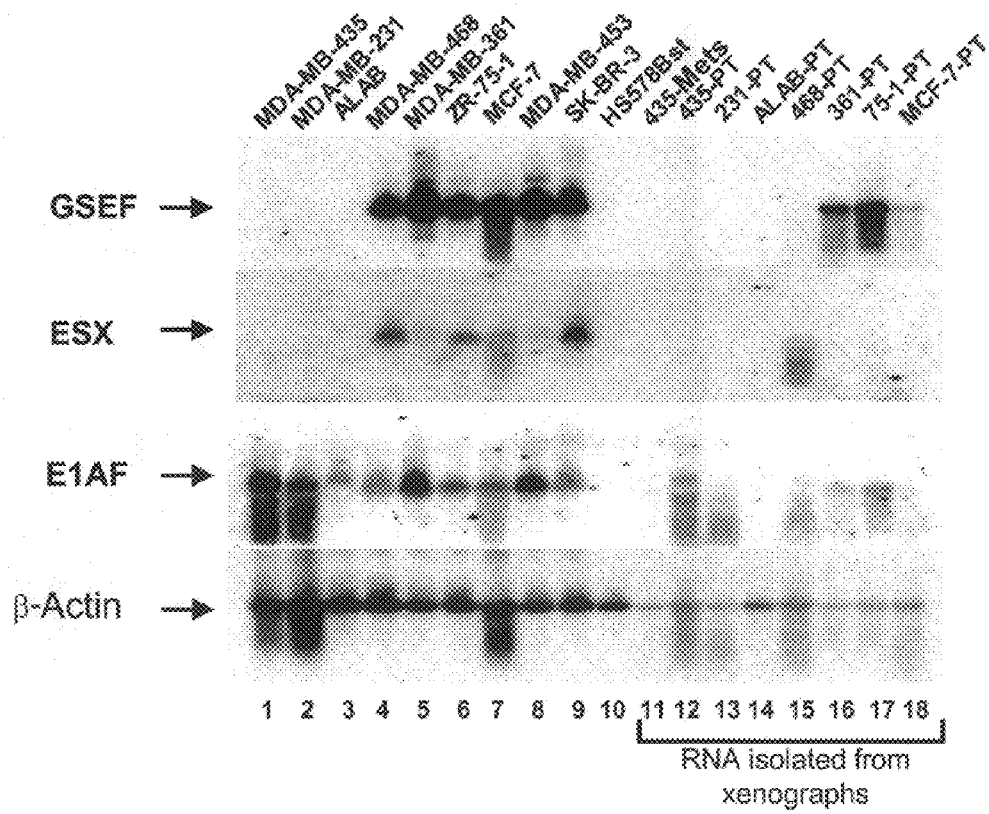
FIG. 5 is a photograph of a Northern blot showing expression of GSEF, ESX, E1AF, and β-actin in using total RNA derived from HBC cell lines or from tumor or metastasis tissue derived from xenographs. Specific signals are indicated by arrows.

The results are shown in FIG. 5, where the upper panel indicates GSEF expression, the second uppermost panel indicates ESX expression, the third panel from the top indicates E1AF expression, and the bottom panel indicates β-actin expression (control). While GSEF expression was detected in both low metastatic potential breast cell lines and in non-metastatic breast cell lines, GSEF expression was substantially undetectable in high metastatic potential breast cell lines in this assay (435, 231, ALAB), indicating a specific loss of function in cell lines with high metastatic potential. The cell line HS578Bst is a cell line derived from breast tissue but has been characterized to be fibroblast-like and did not show any expression whereas the six low metastatic epithelial derived cell lines showed strong expression of GSEF. The same northern blot was probed with an E1AF (PEA3)-specific probe as well as a probe for ESX. E1AF and ESX are both ETS transcription factor implicated in metastasis. Interestingly ESX, an epithelial specific ETS transcription factor, exhibited an expression profile similar to GSEF, whereas E1AF expression was strongest in the two high metastatic cell lines 435 and 231. It should be noted that some ESX and GSEF mRNA was detected by RT PCR in the high metastatic cell lines, suggesting that the absence of expression is not due chromosomal deletions (data not shown). Thus, GSEF expression correlates inversely with the metastatic potential of breast cancer cells. These data further support the role of GSEF in suppression of the metastatic phenotype.

To exclude the possibility that the expression profiles are influenced by in vitro culture conditions, RNA derived from mouse xenograhs was analyzed (FIG. 5, lanes 11 to 18; PT primary tumors, Mets 435 derived lung metastasis). The cell line specific expression of all three ETS transcription factors was maintained in vivo, thus ruling out culture conditions as a cause for the differential expression.

In order to confirm differential gene expression results on the protein level, specific polyclonal antibodies for GSEF, ESX and E1AF were generated and used in an immunoblot analysis. Equal amounts of nuclear extracts derived from each of the breast cell lines described above were loaded on an SDS-PAGE gel and transferred to a PVDF membrane according to methods well known in the art. Polyclonal antibodies raised against a synthetic C-terminal peptide of GSEF (RKPDISQRLVYQFVHPI (SEQ ID NO:6)) and ESX (GKNSSGWKEEEVLQSM (SEQ ID NO:7)) were used to detect the proteins. Ets1 and E1AF were detected using commercially available antibodies.

As shown in FIG. 6, protein expression confirmed the northern data. GSEF protein expression was highly abundant in four of the six low metastatic cell lines but was not detectable in the high metastatic HBC cell lines (FIG. 4). The ESX protein was also restricted to the low metastatic cell lines suggesting a shift into a more nonepithelial like phenotype in the high metastatic cell lines. The immunoblot for E1AF did show a slight upregulation of E1AF protein in the high metastatic cell lines, but was also detectable in some of the low metastatic cell lines. Immunoblots for three additional ETS factors (ERM, Ets2, Ets1) were performed, but did not reveal a significant correlation with the phenotype of these cell lines. Using the Ets2 specific antibody we observed an additional smaller polypeptide specifically in the high metastatic cell lines(second arrow FIG. 4). This shorter Ets2 specific signal was due to a proteolytic activity in the cell extracts derived from the high metastatic cell lines (data not shown).

Taken together, these data illustrate the identification of two Ets transcription factors, GSEF and ESX, which have their expression specifically downregulated during the EMT.

Example 6

GSEF Expression in Human Tumor Tissue

Figure 7A:
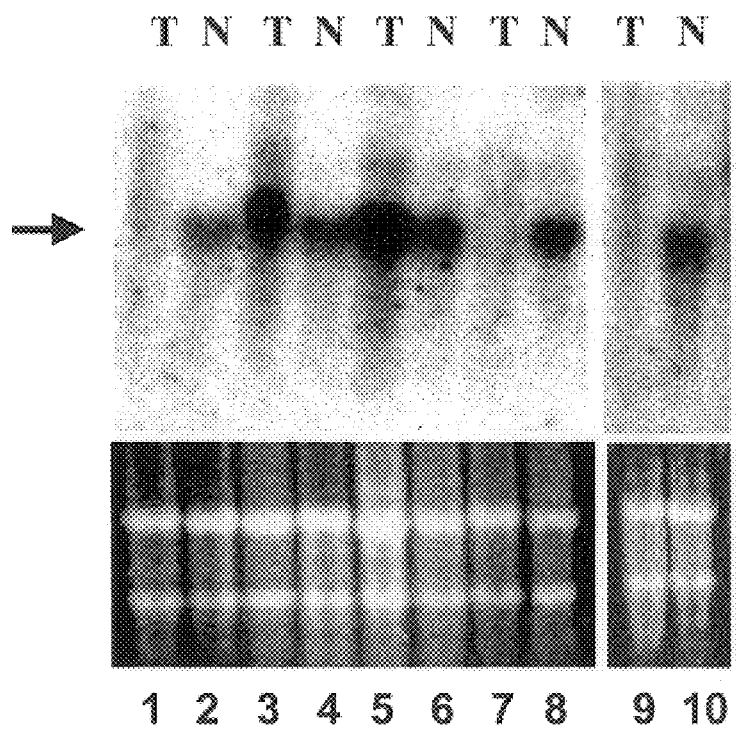
FIG. 7A is a photograph of a Northern blot illustrating that GSEF mRNA is differentially expressed in primary tumor (T) and normal (N) breast tissue. Total RNA from matched normal (even-numbered lanes) and primary tumor (odd-numbered lanes) tissue were used: lane 1: invasive ductal carcinoma; lane 3: invasive ductal carcinoma; lane 5: moderately differentiated invasive ductal carcinoma; lane 7: invasive-ductal carcinoma; lane 9: invasive ductal carcinoma.

In view of the results described above, the expression of GSEF in human breast tumor tissue was investigated in matched total RNA derived from normal and tumor breast tissue. As shown in FIG. 7A, all five patients exhibited comparable expression of GSEF in normal tissue (FIG. 7A, even numbered lanes). Two patients exhibited upregulation of GSEF message in tumor tissue when compared to normal, whereas GSEF expression was undetectable in tumors of three patients. These results illustrate the changes in gene expression of GSEF during the progression of breast cancer.

Expression of GSEF was also examined in human breast tissue in situ. Briefly, in situ hybridization was performed on human tissues frozen immediately after surgical removal and cryosectioned at 10 m, following the protocol of Pfaff et al. (1996) *Cell* 84: 309–320. Digoxigenin-UTP labeled riboprobes were generated with a template containing GSEF cDNA. For the generation of the antisense probe, the DNA was linerarized at the 5'-end and transcribed with T3 polymerase to generate a transcript of approximately 1 kb length. Hybridized probes were detected with alkaline phosphatase-coupled anti-digoxigenin antibodies using BM purple as the substrate (Roch Molecular Biochemicals, Indianapolis, Ind.).

Figure 7B:
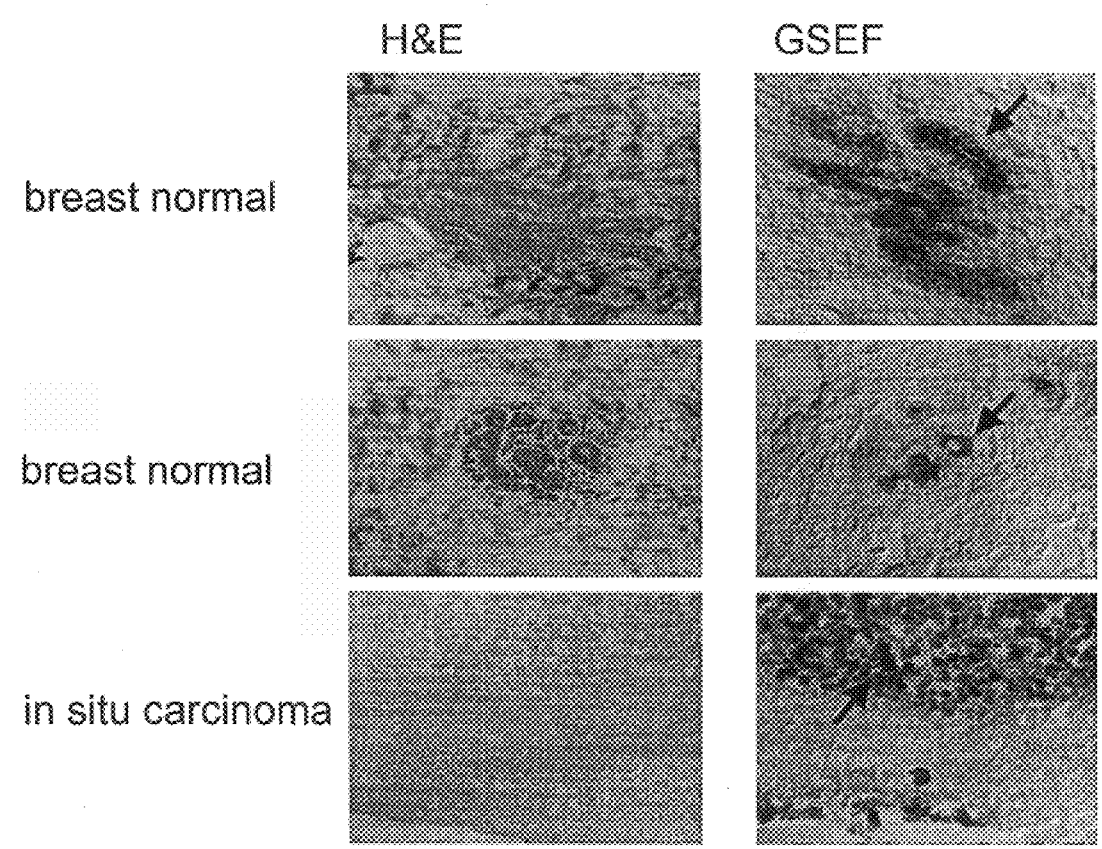
FIG. 7B is a photograph showing the results of in situ hybridization analysis of GSEF in normal and malignant human breast tissue. H&E staining of the same section is shown in the left panel.

As illustrated in the exemplary results provided in FIG. 7B, GSEF is specifically expressed in normal ductal epithelial cells, with expression decreased or undetectable in metastatic breast cancer cells. Thus, GSEF expression was maintained in the in situ carcinoma of the same patient, again correlating with the in vitro gene expression of GSEF in tumorgenic low metastatic HBC cell lines.

Example 7

Chromosomal Mapping of GSEF

The chromosomal location of GSEF was determined by radiation hybrid mapping. The GSEF-specific primers 5'cagggaggggcaaccaactgccccagggggga3' (SEQ ID NO:10) and 5'tatctttattatccattcccgggggcactcctgg3' (SEQ ID NO:11) for PCR reactions on genomic DNA derived from human/hamster hybrid cells (Research Genetics™). The result was analysed by an outside laboratory for the nearest marker (SHGC-15970).

GSEF was mapped to chromosome 6, specifically at 6p21.1–6p21.3. Normal human Chromosome 6 has been implicated in the suppression of the metastatic phenotype of C8161 melanoma after microcell transfer (Welch et al., (1994) *Oncogene* 9:255–262; Barsky et al., (1997) *Oncogene* 15:2077–2091). Interestingly, cyclin-dependent kinase inhibitor 1A (p21/WAF/CDKN1A), which is considered to be a putative tumor suppressor gene, also mapps to 6p21.2 (Knuutila et al., (1999) *Am. J. Pathol.* 155:683–694). Furthermore, it has been suggested that loss of heterozygosity on chromosome 6p21.2 is a potential marker for recurrence after radiotherapie of cervical cancer (Harima et al., (2000) *Clin. Caner Res.*6:1079–1085).

Example 8

Promoter of GSEF

The promoter of GSEF was obtained using the Human Genome Walker Kit™ (Clontech) in combination with PCR primers specific for the GSEF cDNA designed according to methods well known in the art. The resulting PCR products were cloned into TA-cloning vectors (InVitrogen) and double-stand sequenced. The GSEF promoter, as well as the beginning of the cDNA encoding GSEF is provided in SEQ ID NO:8). The sequence of the putative minimal GSEF promoter (e.g., without the GSEF-encoding cDNA sequence) is provided as SEQ ID NO:9 (nucleotides 1–1381 of SEQ ID NO:8). The classic TATA box begins at residue 1356 (TATAA), and a transcriptional start site is positioned at residue 1381.

Example 9

GSEF Promoter and GSEF Protein are Functional in Transient Transfection Assays

In order to characterize the transcriptional regulation of GSEF, a 1380 bp promoter fragment was cloned upstream of a luciferase reporter construct containing either a promoter of c-Fos, a CMV promoter (CMV 10x), a promoter of pGL3, or the GSEF promoter, and transfected into the high metastatic cell line MDA-MB-435 and into two low metastatic cell lines (MDA-MB-468, SK-BR-3) using techniques well known in the art. Cotransfection of luciferase promoters is described in, for example, Martin et al., (1999) Mol. Cell. Biol.: 5548–5556 (c-Fos; CMV promoter).

Figure 8:
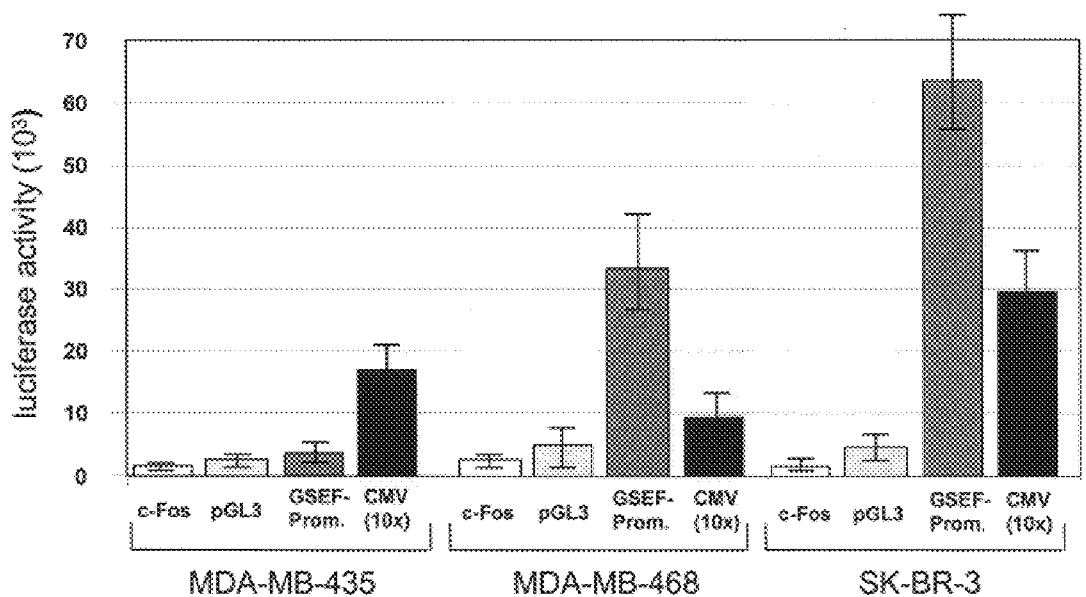
FIG. 8 is a graph illustrating that the activity of the GSEF promoter is greater in low metastatic than in high metastatic HBC cell lines. All promoters are cloned into pGL3 basic luciferase expression plasmid (Promega): pGL-3 promoterless, c-Fos promoter, GSEF-promoter, CMV-promoter(1/10 of the absolute numbers are shown).c-Fos: construct with c-Fos promoter; pGL3; GSEF-Prom: construct with GSEF promoter; CMV (10×): construct with CMV promoter.

The GSEF promoter did not exhibit significant activity in the high metastatic breast cancer cell line MDA-MB-435 (FIG. 8, left panel, compare promoter less pGL3 control with GSEF-promoter construct). However GSEF reporter activity in the low metastatic cell lines increased relative to the CMV, c-FOS and the pGL-3-basic promoter constructs (FIG. 8, absolute luciferase units are shown). This result indicate that the cloned GSEF promoter fragment is sufficient to mediate the low metastatic specific transcriptional regulation and reflects the differential expression of endogenous GSEF.

Example 10

GSEF Acts as a Transcriptional Activator of the GSEF Promoter

The ability of ectopically expressed GSEF protein to act as a transcriptional activator of the GSEF promoter in the high metastatic cell line MDA-MB-435 was investigated. Cotransfection using the indicated reporter constructs in combination with the expression plasmids (pcDNA 3.1) were performed using the EFFECTENE™ transfection reagent (Quiagen) accoding to the manufacturer's protocol (Martin et al., (1999) *Mol. Cell. Biol.* : 5548–5556). GSEF, E1AF, and ESX were expressed in the transfected cells at similar levels as confirmed by Western blot (data not shown).

Figure 9:
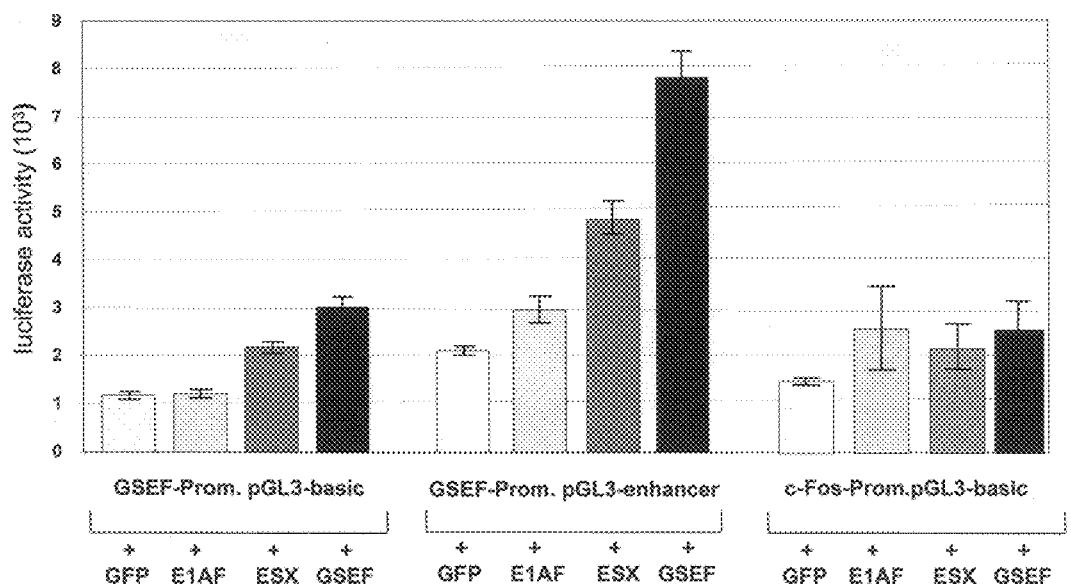
FIG. 9 is a graph illustrating that the GSEF promoter of the GSEF-pGL3-luc construct in the high metastatic breast cell line MDA-MB-435 can be transactivated by GSEF protein. +GFP: GFP expression construct; +E1AF: expression construct; +ESX: ESX expression construct; and GSEF: GSEF expression construct.

Cotransfection of expression plasmids of GSEF, E1AF, ESX and a GFP control revealed that GSEF was the strongest transcriptional transactivator of the GSEF promoter construct (FIG. 9). Both ESX and E1AF also showed some transactivation in these transient transfection assays, which is not surprising given that the GSEF promoter fragment contains a series of ETS binding sites (FIG. 2A, indicated in bold). However the minimal c-Fos promoter was not stimulated by either of these ETS factors.

The activity of GSEF as a transcription factor was confirmed by nuclear localization using immunohistochemistry protocols in combination with DAPI counterstaining (data not shown).

These data indicate that GSEF protein is localized in the nucleus and can function as a transcriptional activator in the high metastatic cell line MDA-MB-435.

Example 11

Ectopic Expression of GSEF Does Not Affect Vimentin or Cytokeratin 19 Expression, but Changes the Morphology of MDA-MB-435 Cells Having established that the GSEF protein can be expressed in a functional manner in high metastatic potential cells, MDA-MB-435 cell lines that stably express GSEF were produced to address whether GSEF expression can interfere with the metastatic phenotype of MDA-MB-435 cells. The expression plasmids(pcDNA.3, Promega) were transfected into MDA-MB-435 cells (EFFECTENE™ (Quiagen)) and the cells were incubated for 1 week under G418 selection (200 µg/ml). Individual clones were picked and analysed.

Figure 10:
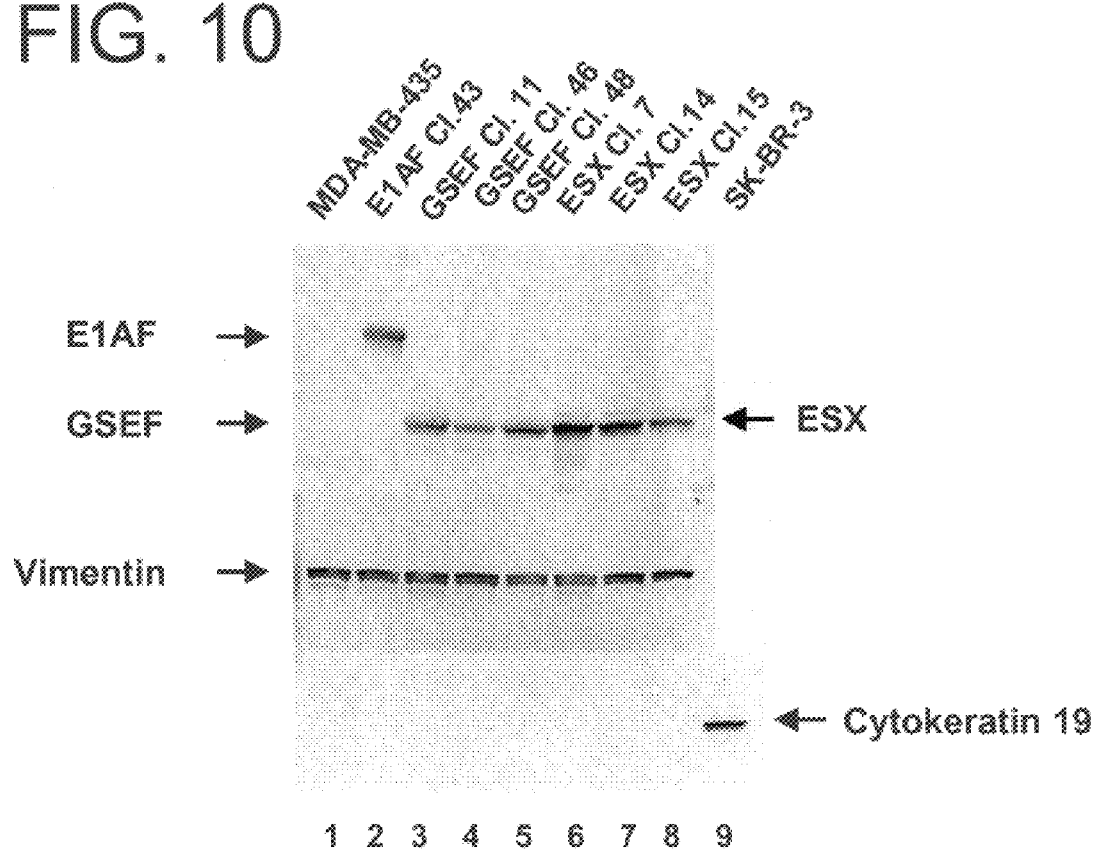
FIG. 10 is a photograph of a Western blot showing the effect of expression of E1AF, GSEF, or ESX upon Vimentin and cytokeratin 19 production in MDA-MB-435 cells.

Expression of GSEF, E1AF, ESX, Vimentin, and Cytokeratin 19 was examined by Western blot of whole cell lysates of MDA-MB-435 cells containing an E1AF expression construct (E1AF Cl.43), MDA-MB-435 cells containing a GSEF expression construct (GSEF Cl.11, GSEF CL.46, and GSEF Cl.48), and MDA-MB-435 cells containing an ESX expression construct (ESX Cl.7, ESX Cl.15, and ESX Cl.15). Whole cell lysates of MDA-MB-435 and SK-BR-3 cells served as controls. Expression of E1AF was used as a negative control since parental MDA-MB-435 cells express endogenous E1AF. As shown in FIG. 10, none of the three ETS transcription factors had an effect on the level of endogenous vimentin and cytokeratin 19 expression.

The effect of GSEF expression upon morphology, anchorage-independent growth (soft agar assay as described previously (Hamburger and Salmon, (1977) Science, 197:461–463), and invasiveness of MDA-MB-435 cells (matrigel assay: 3-dimensional reconstituted basemembrane culture were generated as described previously (Peterson et al., (1992) Proc. Natl. Acad. Sci. USA 89:9064–9068) using a commercially prepared reconstituted basement membrane (Matrigel; Collaborative Research, Waltham, Mass.) was examined using methods well known in the art.

As shown in FIG. 11, expression of GSEF in MDA-MB-435 cells (MDA-MB-GSEF (Cl.46) and MDA-MB-435-GSEF (Cl.48)) had significant effects on cell morphology compared to untransfected cells, and further had even more dramatic effects than stable expression of E1AF (MDA-MB-435-E1AF (Cl.43))

Having established that the GSEF protein can be expressed in a functional manner, stable MDA-MB-435 cell lines were created. These experiments were designed to address the question of whether GSEF expression can interfere with the metastatic phenotype of MDA-MB-435 cells or might have an effect on the differentiation status of these cells. In short, immunoblot analysis was performed according to methods well known in the art to determine the effect of GSEF, E1AF, and ESX on expression of vimentin and cytokeratin 19. As shown in FIG. 10, the MDA-MB-435 cells expressed approximately equal levels of GSEF, E1AF and ESX. An E1AF expression plasmid was used as a negative control since parental MDA-MB-435 cells express endogenous E1AF (see FIG. 5). However, none of the three ETS transcription factor had an effect on the protein expression level of these EMT indicator genes (FIG. 10).

Studies of the morphology of transfected cells revealed that the cell morphology was noticabley different in the GSEF stable transfectant compared to the parental MDA-MB-435 or the E1AF control transfectant (FIG. 11). The characteristic elongated, needle like, morphology of the MDA-MB-435 cells was altered into a more spherical shaped form, lacking the needle like extrusions. Interestingly the morphology of the GSEF stable transfectan more resembled the phenotype of the nontumorigenic SK-BR-3 cells (FIG. 11, uper right panel). The E1AF expressing clones and cells stably transfected with a GFP expression plasmid (data not shown) maintained the needle like structure of MDA-MB-435.

FIG. 12 provides exemplary results of the experiments to test the anchorage-independent growth of GSEF-expressing MDA-MB-435 cells. The stable MDA-MB-435 transfectant was then tested for anchorage-independent cell growth in the presence of serum according to methods well known in the art. Neither of the ectopically expressed Ets transcription factors E1AF or GSEF caused a significant change in the colony formation soft agar assay when compared to the parental MDA-MB-435 cells (FIG. 12). The nontumorigenic SK-BR3 cells serves as a negative control in this assay. These data indicate that ectopically expressed GSEF does not affect nchorage-independent cell growth. However this result was not surprising since two of the low metastatic, tumorigenic HBC cell lines (MCF-7, ZR-75-1) express sigficant amounts of endogenous GSEF (see FIG. 5). Preliminary data using the mammary fat pad mouse model revealed that all stable transfectants retained the capacitiy to form primary tumors (data not shown).

FIG. 13 provides exemplary results of the Matrigel invasion/motility assay to test the invasiveness of GSEF-expressing MDA-MB-435 cells. Again the SK-BR-3 cell line was used as a negative control and did not exhibit any three-dimensional, growth as expected. The parental MDA-MB-435 as well as the E1AF transfectant exhibited characterisitic three dimensional growth pattern indicative of metastatic cells (FIG. 13). Both GSEF transfectants analyzed in this assay proliferated in the Matrigel assay, but clearly lacked the three dimensional growth phenotype. These results indicate that the presence of ectopically expressed GSEF protein suppresses migration and or motility of these cells but has no detectable effect on anchorage independent growth as measured in the above-described assay. In general, these data show that expression of GSEF reduces the invasiveness of MDA-MB-435 cells.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of determining the low metastatic potential of a cell, the method comprising:

detecting a level of a GSEF gene product in a test cell obtained from human breast tissue;

wherein the level of GSEF gene product in a test cell that is significantly higher than a control level of GSEF indicates that the test cell is of low metastatic potential, wherein the control level is a level of GSEF gene product associated with a normal breast cell, a non-malignant breast cancer cell or a high malignant potential breast cancer cell.

2. The method of claim 1, wherein the GSEF gene product is a GSEF polynucleotide.

3. The method of claim 1, wherein said detecting is by hybridization to an array.

4. A method of identifying a cancerous cell of low metastatic potential in human breast tissue, the method comprising the steps of:

detecting a level of a GSEF gene product in a test sample obtained from human breast tissue;

wherein the level of GSEF gene product in a test cell that is significantly higher than a control level of GSEF indicates that the human breast tissue contains a cancerous cell of low metastatic potential, wherein the control level is a level of GSEF gene product associated with a human breast tissue containing normal breast cells, a non-malignant breast cancer cells, a high malignant potential breast cancer cells, or a mixture thereof.

5. The method of claim 4, wherein said detecting is by hybridization to an array.

6. The method of claim 4, wherein the GSEF gene product is a GSEF polynucleotide.

7. A method of determining the high metastatic potential of a cell, the method comprising:

detecting a level of a GSEF gene product in a test cell obtained from human breast tissue;

wherein the level of GSEF gene product in a test cell that is significantly lower than a control level of GSEF indicates that the test cell is of high metastatic potential, wherein the control level is a level of GSEF gene product associated with a normal breast cell, a non-malignant breast cancer cell or a low malignant potential breast cancer cell.

8. The method of claim 7, wherein the GSEF gene product is a GSEF polynucleotide.

9. The method of claim 7, wherein said detecting is by hybridization to an array.

10. A method of identifying a cancerous cell of high metastatic potential in human breast tissue, the method comprising the steps of:

detecting a level of a GSEF gene product in a test sample obtained from human breast tissue;

wherein the level of GSEF gene product in a test cell that is significantly lower than a control level of GSEF indicates that the human breast tissue contains a cancerous cell of high metastatic potential, wherein the control level is a level of GSEF gene product associated with a human breast tissue containing normal breast cells, a non-malignant breast cancer cells, a low malignant potential breast cancer cells, or a mixture thereof.

11. The method of claim 10, wherein the GSEF gene product is a GSEF polynucleotide.

12. The method of claim 10, wherein said detecting is by hybridization to an array.

* * * * *